United States Patent
Tang et al.

(10) Patent No.: US 8,039,241 B2
(45) Date of Patent: Oct. 18, 2011

(54) THERMOSTABLE ALPHA-AMYLASES

(75) Inventors: Lan Tang, Beijing (CN); Wenping Wu, Beijing (CN); Junxin Duan, Beijing (CN); Pia Francke Johannesen, Skovlunde (DK)

(73) Assignee: I Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/755,076

(22) Filed: Apr. 6, 2010

(65) Prior Publication Data

US 2010/0209996 A1    Aug. 19, 2010

Related U.S. Application Data

(60) Continuation of application No. 12/036,806, filed on Feb. 25, 2008, now abandoned, which is a division of application No. 11/671,692, filed on Feb. 6, 2007, now abandoned, which is a continuation of application No. 10/539,396, filed as application No. PCT/DK03/00882 on Dec. 16, 2003, now Pat. No. 7,189,552.

(60) Provisional application No. 60/435,483, filed on Dec. 20, 2002.

(30) Foreign Application Priority Data

Dec. 17, 2002   (DK) .................................. 2002 01928

(51) Int. Cl.
| | |
|---|---|
| *C12N 9/30* | (2006.01) |
| *C12N 9/28* | (2006.01) |
| *C12N 1/20* | (2006.01) |
| *C12N 15/00* | (2006.01) |
| *C12P 19/14* | (2006.01) |
| *C12P 21/06* | (2006.01) |
| *C12P 19/34* | (2006.01) |
| *D06M 16/00* | (2006.01) |
| *C07H 21/04* | (2006.01) |
| *A21D 2/00* | (2006.01) |

(52) U.S. Cl. .......... 435/203; 435/202; 435/99; 435/263; 435/252.3; 435/69.1; 435/91.1; 435/320.1; 426/20; 536/23.2; 536/23.1; 536/23.7

(58) Field of Classification Search .................. 435/203, 435/202, 99, 263, 252.3, 69.1, 91.1, 320.1; 426/20; 536/23.2, 23.1, 23.7
See application file for complete search history.

(56) References Cited

U.S. PATENT DOCUMENTS 7,189,552 B2   3/2007   Lan et al.

FOREIGN PATENT DOCUMENTS

| EP | 0184019 | 6/1986 |
|---|---|---|
| EP | 0238023 | 12/1993 |
| WO | WO 90/11352 | 10/1990 |
| WO | WO 94/19454 | 9/1994 |
| WO | WO 95/10603 | 4/1995 |
| WO | WO 95/26397 | 10/1995 |
| WO | WO 96/01323 | 1/1996 |
| WO | WO 96/23873 | 8/1996 |
| WO | WO 96/23874 | 8/1996 |
| WO | WO 97/35956 | 10/1997 |
| WO | WO 01/04273 | 1/2001 |
| WO | WO 01/34784 | 5/2001 |
| WO | WO 02/068589 | 9/2002 |
| WO | WO 02/068597 | 9/2002 |

OTHER PUBLICATIONS

Ashok et al., Database Biosis, Accession No. PREV20000226835 (2000).
Broun et al., Science, vol. 282, pp. 1315-1317 (1998).
Devos et al., Proteins: Structure, Function, and Genetics, vol. 41, pp. 98-107 (2000).
Guo et al., Procedures of the National Academy of Sciences of the United States of America, vol. 101, No. 25, pp. 9205-9210 (2004).
Okada et al, Protein Experimentation Notes, Second vol., to Determination of Primary Structure Mighty Biotechnical Series (1998).
Seffernick et al., Journal of. Bacteriology, vol. 183, No. 8, pp. 2405-2410 (2001).
Somkuti et al., Developments in Industrial Microbiology, vol. 21, pp. 327-337 (1979).
Turchi et al., Current Microbiology, vol. 15, pp. 203-205 (1987).
Whisstock et al., Quarterly Reviews of Biophysics, vol. 36, No. 3, pp. 307-340 (2003).
Witkowski et al., Biochemistry, vol. 38, pp. 11643-11650 (1999).

*Primary Examiner* — Ganapathirama Raghu
(74) *Attorney, Agent, or Firm* — Elias Lambiris

(57) ABSTRACT

The present invention relates to an isolated polynucleotide comprising an open reading frame encoding a polypeptide having alpha-amylase activity, the polypeptide selected from the group consisting of:
  a) a polypeptide comprising an amino acid sequence which has at least 70% identity with amino acids 1 to 450 of SEQ ID NO: 4;
  b) a polypeptide comprising an amino acid sequence which has at least 70% identity with the polypeptide encoded by the amylase encoding part of the polynucleotide inserted into a plasmid present in the *E. coli* host deposited under the Budapest Treaty with DSMZ under accession number DSM 15334;
  c) a polypeptide encoded by a polynucleotide comprising a nucleotide sequence which has at least 70% identity with the sequence shown from position 68 to 1417 in SEQ ID NO: 3; and
  d) a fragment of (a), (b) or (c) that has alpha-amylase activity.

18 Claims, 14 Drawing Sheets

THERMOSTABLE ALPHA-AMYLASES

CROSS-REFERENCE TO RELATED APPLICATIONS

This application is a continuation of U.S. application Ser. No. 12/036,806 filed Feb. 25, 2008, now abandoned, which is a divisional of U.S. application Ser. No. 11/671,692 filed Feb. 6, 2007, now abandoned, which is a divisional of U.S. application Ser. No. 10/539,396 filed Jun. 16, 2005, now U.S. Pat. No. 7,189,552, which is a national phase application under 35 U.S.C. 371 of PCT/DK2003/00882 filed Dec. 16, 2003, which claims priority or the benefit under 35 U.S.C. 119 of Danish application No. PA 2002 01928 filed Dec. 17, 2002 and U.S. provisional application No. 60/435,483 filed Dec. 20, 2002, the contents of which are fully incorporated herein by reference.

FIELD OF THE INVENTION

The present invention relates to thermostable alpha-amylases, in particular with improved thermal stability at acidic pH. The invention also relates to the use of such alpha-amylases.

BACKGROUND OF THE INVENTION

Alpha-Amylases (alpha-1,4-glucan-4-glucanohydrolases, EC. 3.2.1.1) constitute a group of enzymes which catalyze hydrolysis of starch and other linear and branched 1,4-glucosidic oligo- and polysaccharides.

There is a very extensive body of patent and scientific literature relating to this industrially very important class of enzymes. A number of alpha-amylases referred to as "TER-MAMYL®-like alpha-amylases" and variants thereof are known from, e.g., WO 90/11352, WO 95/10603, WO 95/26397, WO 96/23873 and WO 96/23874. TER-MAMYL®-like alpha-amylases are very thermostable and therefore suitable for processes carried out at high temperatures such as starch liquefaction in dextrose production processes.

Another group of alpha-amylases are referred to as "FUN-GAMYL™-like alpha-amylases", which are alpha-amylases related or homologous to the alpha-amylase derived from *Aspergillus oryzae*. The FUNGAMYL™-like alpha-amylases have a relatively low thermostability the commercial product sold under the tradename FUNGAMYL™ by Novozymes A/S, Denmark, has a optimum around 55° C., and is not suitable for processes carried out at high temperatures. FUNGAMYL™-like alpha-amylases are today used for making syrups for, e.g., the brewing industry.

Clearly, it would be advantageous to provide an alpha-amylase with increased thermostability preferably at an acidic pH. This is no new realization, but actually a very long-felt need in the art. As far back as in 1980, Somkuti and Steinberg described a thermoacidophilic extracellular alpha-amylase of Rhizomucor pusillus (Mucor pusillus), that they managed to isolate and characterize. They state that: "Since high temp and acidic pH are optimum conditions for the economic hydrolysis of starch, the use of thermostable and acid-stable amylases of microbial origin for industrial purposes has been recommended", and go on to conclude about the Rhizomucor amylase that: "It is apparently the first example of fungal alpha-amylase exhibiting both acidophily and thermophily simultaneously. Consequently, the alpha-amylase of M.pusillus should be of economic importance." (Somkuti and Steinberg, 1980, "Thermoacidophilic extracellular amylase of Mucor pusillus", *Dev. Indust. Microbiol.* 21:327-337).

However, despite the very clear conclusions by Somkuti and Steinberg back in 1980, the gene encoding the Rhizomucor pusillus alpha-amylase had until today not been cloned or sequenced, and the amylase had until today not been produced recombinantly in industrially relevant amounts. In 1987 an improved purification method was reported, but still only for enzyme produced by the wild-type Rhizomucor pusillus (Turchi and Becker, 1987, *Curr. Microbiol.* 15:203-205).

SUMMARY OF THE INVENTION

A problem to be solved by this invention is how to provide a recombinant thermoacidophilic alpha-amylase. The present inventors have successfully isolated a gene from Rhizomucor pusillus encoding an alpha-amylase which they have denoted AM782, they have successfully introduced the encoding gene into a recombinant industrial filamentous fungal expression system, and produced the alpha-amylase. Characterization of the amylase has shown it to be a highly thermoacidophilic alpha-amylase which has a highly interesting activity as demonstrated by the sugar profile from maltodextrin hydrolysis by amylase AM782.

The amylase AM782 can work at a very high temperature, at least up to 70° C. The amylase AM782 has a very fast reaction speed; when compared at the same dosage with Fungamyl™ 800 L, the amylase AM782 can achieve in about 3 hours, what takes Fungamyl™ 24 to 48 hours. Furthermore, the amylase AM782 can degrade DP3 into DP2 and DP1, so it gives a higher DP1 result.

Accordingly, in a first aspect the invention relates to an isolated polynucleotide comprising an open reading frame encoding a polypeptide having alpha-amylase activity, the polypeptide selected from the group consisting of: a) a polypeptide comprising an amino acid sequence which has at least 70% identity with amino acids 1 to 450 of SEQ ID NO: 4, preferably 75%, more preferably 80%, even more preferably 85%, still more preferably 90%, more preferably 95%, and most preferably at least 97% identity with amino acids 1 to 450 of SEQ ID NO: 4; b) a polypeptide comprising an amino acid sequence which has at least 70% identity with the polypeptide encoded by the amylase encoding part of the polynucleotide inserted into a plasmid present in the *E. coli* host deposited under the Budapest Treaty with DSMZ under accession number DSM 15334, preferably 75%, more preferably 80%, even more preferably 85%, still more preferably 90%, more preferably 95%, and most preferably at least 97% identity with the polypeptide encoded by the amylase encoding part of the polynucleotide inserted into a plasmid present in the *E. coli* host deposited under the Budapest Treaty with DSMZ under accession number DSM 15334; c) a polypeptide encoded by a polynucleotide comprising a nucleotide sequence which has at least 70% identity with the sequence shown from position 68 to 1417 in SEQ ID NO: 3, preferably 75%, more preferably 80%, even more preferably 85%, still more preferably 90%, more preferably 95%, and most preferably at least 97% identity with the sequence shown from position 68 to 1417 in SEQ ID NO: 3; and d) a fragment of (a), (b) or (c) that has alpha-amylase activity.

In a second aspect the invention relates to a nucleic acid construct comprising a polynucleotide as defined in the first aspect operably linked to one or more control sequences that direct the production of the polypeptide in a suitable host.

A third aspect relates to a recombinant expression vector comprising a nucleic acid construct as defined in the second aspect.

In a fourth aspect the invention relates to a recombinant host cell comprising a nucleic acid construct as defined in the second aspect, or at least one copy of an expression vector as defined in the third aspect.

Industrial production of the amylase AM782 along with homologues and variants is of course highly interesting.

Accordingly, in a fifth aspect the invention relates to a method for producing a polypeptide having alpha-amylase activity encoded by a polynucleotide as defined in the first aspect, the method comprising: (a) cultivating a recombinant host cell as defined in any of claims 12-16 under conditions conducive for production of the polypeptide; and (b) recovering the polypeptide.

There are quite a few applications for an amylase such as the amylase AM782, an overview of some of the major ones is given herein, and it includes but is not limited to: the starch industry, the food processing industry, the textile industry, and the detergent industry.

Consequently, additional aspects of the invention relate to a method of producing an enzymatically modified starch derivative, wherein a polypeptide having alpha-amylase activity produced according to a method as defined in the fifth aspect is used for liquefying and/or saccharifying starch; and to a method of producing high maltose syrups, wherein a polypeptide having alpha-amylase activity produced according to a method as defined in the fifth aspect is used for liquefying starch; a method for desizing textile, wherein a polypeptide having alpha-amylase activity produced according to a method as defined in the fifth aspect is used for treating the textile; and to a brewing process, wherein a polypeptide having alpha-amylase activity produced according to a method as defined in the fifth aspect is added during fermentation of wort; and to an alcohol production process, wherein a polypeptide having alpha-amylase activity produced according to a method as defined in the fifth aspect is used for liquefaction starch in a distillery mash; and to a process, wherein a dough product comprising a polypeptide having alpha-amylase activity produced according to a method as defined in the fifth aspect is baked.

Various uses of amylase AM782 along with homologues and variants are also contemplated in the present invention.

Accordingly, a number of non-limiting aspects of the invention relate to the use of a polypeptide having alpha-amylase activity produced according to a method as defined in the fifth aspect in a starch conversion process for liquefaction and/or saccharification; to the use of a polypeptide having alpha-amylase activity produced according to a method as defined in the fifth aspect for liquefying starch in a high maltose syrup production process; to the use of a polypeptide having alpha-amylase activity produced according to a method as defined in the fifth aspect for textile desizing; to the use of a polypeptide having alpha-amylase activity produced according to a method as defined in the fifth aspect for producing alcohol; to the use of a polypeptide having alpha-amylase activity produced according to a method as defined in the fifth aspect for brewing; and to the use of a polypeptide having alpha-amylase activity produced according to a method as defined in the fifth aspect for baking.

BRIEF DESCRIPTION OF THE DRAWINGS

FIG. 3-1 shows the stability of the amylases AM782, FUNGAMYL™ and BAN at pH 5.0 at 60° C.

FIG. 3-2 shows the stability of the amylases AM782, FUNGAMYL™ and BAN at pH 5.0 at 70° C.

FIG. 3-3 shows the stability of the amylases AM782, FUNGAMYL™ and BAN at pH 5.0 at 80° C.

FIG. 4-1 shows the stability of the amylases AM782, FUNGAMYL™ and BAN at pH 5.0 at 60° C.

FIG. 4-2 shows the stability of the amylases AM782, FUNGAMYL™ and BAN at pH 5.0 at 70° C.

FIG. 4-3 shows the stability of the amylases AM782, FUNGAMYL™ and BAN at pH 5.0 at 80° C.

FIG. 5-1 shows the stability of the amylases AM782, FUNGAMYL™ and BAN at pH 5.0 at 60° C.

FIG. 5-2 shows the stability of the amylases AM782, FUNGAMYL™ and BAN at pH 5.0 at 70° C.

FIG. 5-3 shows the stability of the amylases AM782, FUNGAMYL™ and BAN at pH 5.0 at 80° C.

DEFINITIONS

Sequence Homology and Alignment

Figure 1:
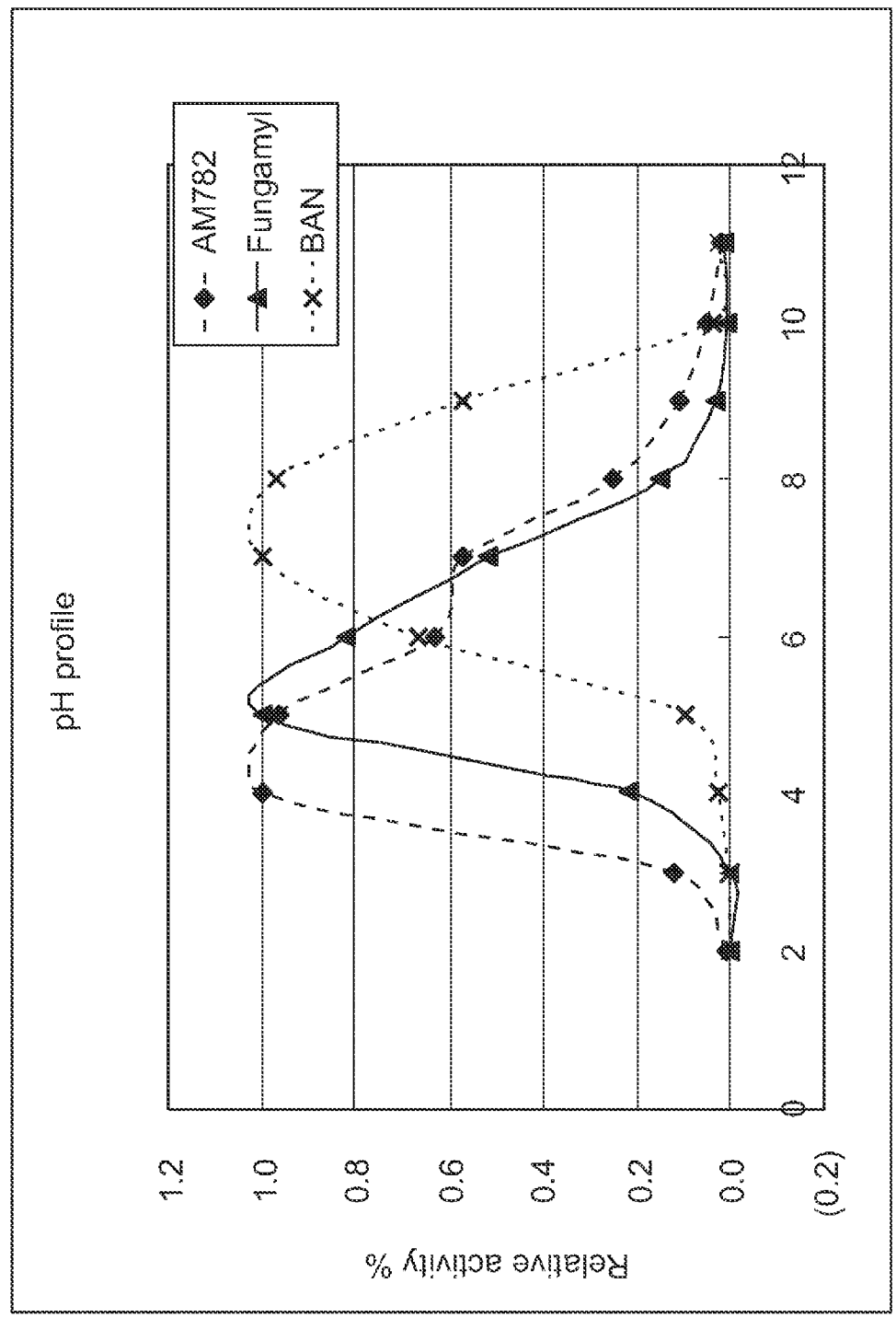
FIG. 1 shows the pH profiles of the amylases AM782, FUNGAMYL™ and BAN.

For purposes of the present invention, alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6 (Pearson and Lipman, 1988, "Improved Tools for Biological Sequence Analysis", *PNAS* 85:2444-2448, and Pearson, 1990, "Rapid and Sensitive Sequence Comparison with FASTP and FASTA", *Methods in Enzymology* 183:63-98).

Multiple alignments of protein sequences may be made using "ClustalW" (Thompson, Higgins, and Gibson, 1994, "CLUSTAL W: improving the sensitivity of progressive multiple sequence alignment through sequence weighting, positions-specific gap penalties and weight matrix choice", *Nucleic Acids Research* 22:4673-4680). Multiple alignment of DNA sequences may be done using the protein alignment as a template, replacing the amino acids with the corresponding codon from the DNA sequence.

Substantially Pure Polynucleotide

The term "substantially pure polynucleotide" as used herein refers to a polynucleotide preparation, wherein the polynucleotide has been removed from its natural genetic milieu, and is thus free of other extraneous or unwanted coding sequences and is in a form suitable for use within genetically engineered protein production systems. Thus, a substantially pure polynucleotide contains at the most 10% by weight of other polynucleotide material with which it is natively associated (lower percentages of other polynucleotide material are preferred, e.g., at the most 8% by weight, at the most 6% by weight, at the most 5% by weight, at the most 4% at the most 3% by weight, at the most 2% by weight, at the most 1% by weight, and at the most ½% weight). A substantially pure polynucleotide may, however, include naturally occurring 5' and 3' untranslated regions, such as promoters and terminators. It is preferred that the substantially pure polynucleotide is at least 92% pure, i.e., that the polynucleotide constitutes at least 92% by weight of the total polynucleotide material present in the preparation, and higher percentages are preferred such as at least 94% pure, at least 95% pure, at least 96% pure, at least 96% pure, at least 97% pure, at least 98% pure, at least 99%, and at the most 99.5% pure. The polynucleotides disclosed herein are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form".

cDNA

The term "cDNA" when used in the present context, is intended to cover a DNA molecule which can be prepared by reverse transcription from a mature, spliced, mRNA molecule derived from a eukaryotic cell. cDNA lacks the intron sequences that are usually present in the corresponding genomic DNA. The initial, primary RNA transcript is a precursor to mRNA and it goes through a series of processing events before appearing as mature spliced mRNA. These events include the removal of intron sequences by a process called splicing. When cDNA is derived from mRNA it therefore lacks intron sequences.

DETAILED DESCRIPTION OF THE INVENTION

The first aspect of the invention relates to an isolated polynucleotide comprising an open reading frame encoding a polypeptide having alpha-amylase activity, the polypeptide selected from the group consisting of: a) a polypeptide comprising an amino acid sequence which has at least 70% identity with amino acids 1 to 450 of SEQ ID NO: 4; b) a polypeptide comprising an amino acid sequence which has at least 70% identity with the polypeptide encoded by the amylase encoding part of the polynucleotide inserted into a plasmid present in the *E. coli* host deposited under the Budapest Treaty with DSMZ under accession number DSM 15334; c) a polypeptide encoded by a polynucleotide comprising a nucleotide sequence which has at least 70% identity with the sequence shown from position 68 to 1417 in SEQ ID NO: 3; and d) a fragment of (a), (b) or (c) that has alpha-amylase activity.

The techniques used to isolate or clone a nucleotide sequence encoding a polypeptide are known in the art and include isolation from genomic DNA, preparation from cDNA, or a combination thereof. The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other amplification procedures such as ligase chain reaction (LCR), ligated activated transcription (LAT) and nucleotide sequence-based amplification (NASBA) may be used. The nucleotide sequence may be cloned from a strain of Rhizomucor, or another related organism and thus, for example, may be an allelic or species variant of the polypeptide encoding region of the nucleotide sequence.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

The term "polypeptide variant", "protein variant", "enzyme variant", or simply "variant" refers to a polypeptide of the invention comprising one or more alteration(s), such as substitution(s), insertion(s), deletion(s), and/or truncation(s) of one or more specific amino acid residue(s) in one or more specific position(s) in the polypeptide. The total number of such alterations is typically not more than 10, e.g., one, two, three, four, five, six, seven, eight, or nine of said alterations. In addition, the variant of the invention may include other modifications of the parent enzyme, typically not more than 10, e.g., not more than 5 such modifications. The variant generally has a degree of sequence identity with the parent polypeptide of at least 80%, e.g., at least 85%, typically at least 90%, or at least 95%.

The term "parent polypeptide", "parent protein", "parent enzyme", "standard enzyme", or simply "parent" refers to the polypeptide on which the variant was based. This term also refers to the polypeptide with which a variant is compared and aligned. The parent may be a naturally occurring (wild-type) polypeptide, or it may in turn even be a variant thereof, prepared by any suitable means. For instance, the parent protein may be a variant of a naturally occurring polypeptide which has been modified or altered in the amino acid sequence. A parent may also be an allelic variant which is any of two or more alternative forms of a gene occupying the same chromosomal locus. Allelic variation arises naturally through mutation, and may result in polymorphism within populations as is well-described in the art. An allelic variant of a polypeptide is a polypeptide encoded by the corresponding allelic variant of a gene.

The term "randomized library", "variant library", or simply "library" refers to a library of variant polypeptides. Diversity in the variant library can be generated via mutagenesis of the genes encoding the variants at the DNA triplet level, such that individual codons are variegated, e.g., by using primers of partially randomized sequence in a PCR reaction. Several techniques have been described, by which one can create a diverse combinatorial library by variegating several nucleotide positions in a gene and recombining them, for instance where these positions are too far apart to be covered by a single (spiked or doped) oligonucleotide primer. These techniques include the use of in vivo recombination of the individually diversified gene segments as described in WO 97/07205 on page 3, lines 8 to 29 (Novozymes NS). They also include the use of DNA shuffling techniques to create a library of full length genes, wherein several gene segments are combined, and wherein each segment may be diversified, e.g., by spiked mutagenesis (Stemmer, 1994, *Nature* 370: 389-391, and U.S. Pat. Nos. 5,605,793; 5,811,238; and 5,830,721). One can use a gene encoding a protein "backbone" (wild-type parent polypeptide) as a template polynucleotide, and combine this with one or more single or double-stranded oligonucleotides as described in WO 98/41623 and in WO 98/41622 (Novozymes NS). The single-stranded oligonucleotides could be partially randomized during synthesis. The double-stranded oligonucleotides could be PCR products incorporating diversity in a specific region. In both cases, one can dilute the diversity with corresponding segments encoding the sequence of the backbone protein in order to limit the average number of changes that are introduced.

Methods have also been established for designing the ratios of nucleotide mixtures (A; C; T; G) to be inserted in specific codon positions during oligo- or polynucleotide synthesis, so as to introduce a bias in order to approximate a desired frequency distribution towards a set of one or more desired amino acids that will be encoded by the particular codons. It may be of interest to produce a variant library that comprises permutations of a number of known amino acid modifications in different locations in the primary sequence of the polypeptide. These could be introduced post-translationally or by chemical modification sites, or they could be introduced through mutations in the encoding genes. The modifications by themselves may previously have been proven beneficial for one reason or another (e.g., decreasing antigenicity, or improving specific activity, performance, stability, or other characteristics). In such instances, it may be desirable first to create a library of diverse combinations of known sequences. For example, if twelve individual mutations are known, one could combine (at least) twelve segments of the parent protein encoding gene, wherein each segment is present in two forms: one with, and one without the desired mutation. By varying the relative amounts of those segments, one could design a library (of size 212) for which the average number of mutations per gene can be predicted. This can be a useful way of combining mutations, that by themselves give some, but not sufficient effect, without resorting to very large libraries, as is often the case when using 'spiked mutagenesis'. Another way to combine these 'known mutations' could be by using family shuffling of oligomeric DNA encoding the known mutations with fragments of the full length wild type sequence.

Accordingly, a preferred embodiment of the invention relates to a polynucleotide of the first aspect, wherein the polypeptide is an artificial variant comprising an amino acid sequence that has one or more truncation(s), and/or at least one substitution, deletion, and/or insertion of an amino acid as compared to amino acids 1 to 450 of SEQ ID NO: 4.

It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for amylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl which is specific for methylated and hemimethylated DNA to digest the parental DNA template and to select for mutation-containing synthesized DNA. Other procedures known in the art may also be used. For a general description of nucleotide substitution, see, e.g., Ford et al., 1991, *Protein Expression and Purification* 2: 95-107.

Another preferred embodiment relates to a polynucleotide of the first aspect, wherein the polypeptide comprises an amino acid sequence which has at least 70% identity with amino acids 1 to 450 of SEQ ID NO: 4, preferably at least 75%, more preferably 80%, still more preferably 85%, still even more preferably 90%, more preferably 95%, and most preferably at least 97% identity with amino acids 1 to 450 of SEQ ID NO: 4.

Yet another preferred embodiment relates to a polynucleotide of the first aspect, wherein the polypeptide comprises the amino acids 1 to 450 of SEQ ID NO: 4.

In a preferred embodiment the invention relates to a polynucleotide of the first aspect, wherein the polypeptide consists of the amino acids 1 to 450 of SEQ ID NO: 4.

Still another preferred embodiment the invention relates to a polynucleotide of the first aspect, wherein the polypeptide comprises an amino acid sequence which has at least 70% identity with the polypeptide encoded by the amylase encoding part of the nucleotide sequence inserted into a plasmid present in the *E. coli* host deposited under the Budapest Treaty with DSMZ under accession number DSM 15334, preferably at least 80% identity, at least 85% identity, at least 90% identity, at least 95% identity, or at least 97% identity with the polypeptide encoded by the amylase encoding part of the nucleotide sequence inserted into a plasmid present in the *E. coli* host deposited under the Budapest Treaty with DSMZ under accession number DSM 15334; preferably the polypeptide comprises the amino acid sequence encoded by the amylase encoding part of the nucleotide sequence inserted into a plasmid present in the *E. coli* host deposited under the Budapest Treaty with DSMZ under accession number DSM 15334; still more preferably the polypeptide consists of the amino acid sequence encoded by the amylase encoding part of the nucleotide sequence inserted into a plasmid present in the *E. coli* host deposited under the Budapest Treaty with DSMZ under accession number DSM 15334.

Another preferred embodiment relates to the polynucleotide of the first aspect, wherein the polypeptide is an artificial variant which comprises an amino acid sequence that has one or more truncation(s), and/or at least one substitution, deletion, and/or insertion of an amino acid as compared to the amino acid sequence encoded by the amylase encoding part of the nucleotide sequence inserted into a plasmid present in the *E. coli* host deposited under the Budapest Treaty with DSMZ under accession number DSM 15334.

Nucleic Acid Construct

When used herein, the term "nucleic acid construct" means a nucleic acid molecule, either single- or double-stranded, which is isolated from a naturally occurring gene or which has been modified to contain segments of nucleic acids in a manner that would not otherwise exist in nature.

The term nucleic acid construct is synonymous with the term "expression cassette" when the nucleic acid construct contains the control sequences required for expression of a coding sequence of the present invention. A polynucleotide sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" is defined herein as a configuration in which a control sequence is appropriately placed at a position relative to the coding sequence of the DNA sequence such that the control sequence directs the expression of a polypeptide.

When used herein the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes DNA, cDNA, and recombinant nucleotide sequences.

An aspect of the invention relates to a nucleic acid construct comprising a polynucleotide as defined in the first aspect operably linked to one or more control sequences that direct the production of the polypeptide in a suitable host.
Expression Vector In the present context, the term "expression" includes any step involved in the production of the polypeptide including, but not limited to, transcription, post-transcriptional modification, translation, post-translational modification, and secretion.

In the present context, the term "expression vector" covers a DNA molecule, linear or circular, that comprises a segment encoding a polypeptide of the invention, and which is operably linked to additional segments that provide for its transcription.

An aspect of the invention relates to a recombinant expression vector comprising a nucleic acid construct as defined in the previous aspect.

According to the invention, a polynucleotide encoding an amylase of the invention can be expressed using an expression vector which typically includes control sequences such as a promoter, an operator, a ribosome binding site, a translation initiation signal, and optionally a repressor gene, or various activator genes. The recombinant expression vector carrying the polynucleotide encoding an alpha-amylase of the invention may be any vector which can be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

The procedures used to ligate the DNA construct of the invention encoding a glucoamylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, non-limiting examples of useful promoters are those derived from the gene encoding *A. oryzae* TAKA amylase, the TPI (triose phosphate isomerase) promoter from *S. cerevisiae* (Alber et al., 1982, *J. Mol. Appl. Genet.* 1: 419-434, Rhizomucor miehei aspartic proteinase, *A. niger* neutral alpha-amylase, *A. niger* acid stable alpha-amylase, *A. niger* glucoamylase, Rhizomucor miehei lipase, *A. oryzae* alkaline protease, *A. oryzae* triose phosphate isomerase or *A. nidulans* acetamidase, and mutated, truncated, and/or hybrid promoters thereof.

Examples of preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In filamentous fungi, the TAKA alpha-amylase promoter, *Aspergillus niger* glucoamylase promoter, and *Aspergillus oryzae* glucoamylase promoter may be used as regulatory sequences.

Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*. An example of a sequence ensuring autonomous maintenance in a filamentous fungal host cell is the AMA1 sequence. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

Host Cells

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are Gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram-negative bacteria such as *E. coli*. The transformation of the bacteria may, for instance, be effected by protoplast transformation or by using competent cells in a manner known per se.

The host cell may also be a filamentous fungus, e.g., a strain belonging to a species of *Aspergillus*, most preferably *Aspergillus oryzae* or *Aspergillus niger*, or a strain of *Fusarium*, such as a strain of *Fusarium oxysporium, Fusarium graminearum* (in the perfect state named *Gibberella zeae*, previously Sphaeria zeae, synonym with *Gibberella roseum* and *Gibberella roseum* f. sp. cerealis), or *Fusarium sulphureum* (in the prefect state named Gibberella puricaris, synonym with *Fusarium trichothecioides, Fusarium bactridioides, Fusarium sambucium, Fusarium roseum*, and *Fusarium roseum* var. graminearum), *Fusarium cerealis* (synonym with *Fusarium crokkwellnse*), or *Fusarium venenatum*.

In a preferred embodiment of the invention the host cell is a protease deficient or protease minus strain. This may for instance be the protease deficient strain of the genus *Aspergillus*, in particular a strain of *A. oryzae*, such as *A. oryzae* JaL125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of *Aspergillus* as a host micro-organism is described in EP 0238023 (Novo Nordisk), the contents of which are hereby incorporated by reference.

An aspect of the invention relates to a recombinant host cell comprising a nucleic acid construct as defined above, or at least one copy of an expression vector as defined above.

A preferred embodiment relates to a cell of the previous aspect, which is a microorganism; preferably a cell which is a bacterium or a fungus; more preferably a cell which is a gram-positive bacterium such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus* or *Bacillus thuringiensis*; or most preferably a cell which is a protease deficient strain of the fungus *Aspergillus*, in particular *A. oryzae*.

Method of Producing an Alpha-Amylase Variant of the Invention

In a yet further aspect, the present invention relates to a method of producing an alpha-amylase variant of the invention, which method comprises cultivating a host cell under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Various methods for using such produced amylases, as well as more specific uses are outlined in other aspects of the invention as already mentioned in the summary of this invention.

The present invention provides a method of using alpha-amylase encoded by the polynucleotides of the invention for producing glucose or maltose or the like from starch.

Generally, the method includes the steps of partially hydrolyzing precursor starch in the presence of alpha-amylase and then further hydrolyzing the release of D-glucose from the non-reducing ends of the starch or related oligo- and polysaccharide molecules in the presence of glucoamylase by cleaving alpha-1,4 and alpha-1, 6 glucosidic bonds.

The partial hydrolysis of the precursor starch utilizing alpha-amylase provides an initial breakdown of the starch molecules by hydrolyzing internal alpha-(1,4)-linkages. In commercial applications, the initial hydrolysis using alpha-amylase is run at a temperature of approximately 105° C. A very high starch concentration is processed, usually 30% to 40% dry-solids. The initial hydrolysis is usually carried out for approx. five minutes at this elevated temperature. The partially hydrolyzed starch can then be transferred to a second tank and incubated for approximately one hour at a temperature of 85° to 90° C. to derive a dextrose equivalent (D.E.) of 10 to 15.

The step of further hydrolyzing the release of D-glucose from the non-reducing ends of the starch or related oligo- and polysaccharides molecules in the presence of glucoamylase is normally carried out in a separate tank at a reduced temperature between 30 and 60° C. Preferably the temperature of the substrate liquid is dropped to between 55 and 60° C. The pH of the solution is dropped from 6-6.5 to a range between 3 and 5.5. Preferably, the pH of the solution is 4 to 4.5. The glucoamylase is added to the solution and the reaction is carried out for 24-72 hours, preferably 36-48 hours.

The alpha-amylases encoded by the polynucleotides of the invention may also be used in brewing processes. Further, the alpha-amylase encoded by the polynucleotides of the invention may be used for maltose production. High maltose syrup is typically produced as follows.

To produce "High Maltose Syrup" (containing 50-55% maltose), starch is liquefied to DE 10-20. The pH and temperature of the liquefied starch is adjusted to 65° C. and to a pH around 5.0, respectively, and is subjected to maltogenic alpha-amylase activity (e.g., *Bacillus stearothermophilus* amylase, such as Maltogenase™ 4000 L, 0.4 l/t DS (Novozymes)), pullulanase activity (e.g., *Bacillus pullulanase*, such as Promozyme™ 600 L, 0.3 l/t DS (Novozymes)) and alpha-amylase activity (e.g., BAN 240 L or Termamyl™ 120 L, type LS, 0.4 kg/t DS (Novozymes)) for 24-41 hours. The specific process time depends on the desired saccharide spectrum to be achieved. By increasing the dosage of the maltogenic alpha-amylase and pullulanase the maltose content can be increased.

Alternatively, "High Maltose Syrup" may be produced by first liquefying starch to DE 10-20 and then adjusting the pH and temperature to 55° C. or higher and a pH around 5.5 or lower, and then subjecting the liquefied starch to a fungal alpha-amylase activity (e.g., *Bacillus stearothermophilus* amylase, such as Fungamyl™ 800 L (Novozymes)) for 22-44 hours. The dosage of fungal Fungamyl™ 800 L depends on the saccharification time foreseen, e.g., 200 g/t DS for 44 hours and 400 g/t DS for 22 hours. The alpha-amylases encoded by the polynucleotides of the invention may substitute the Fungamyl™ 800 L in the above process, and then the temperature can be even higher, and the pH even lower, resulting in a faster conversion rate, and thus a better overall economy.

To produce "High Maltose Syrup" starch with maltose content of 55-65% starch is liquefied to DE 10-20. The temperature and pH of the liquefied starch is adjusted to 60° C. or higher, and to a pH around 6 or lower, and is subjected to maltogenic alpha-amylase activity (e.g., Maltogenase™ 4000 L, 0.25-1.0 l/t DS (Novozymes)), and fungal alpha-amylase activity (e.g., *Aspergillus* amylase, such as Fungamyl™ 800 L, 0.4-1.0 kg/t DS (Novo Nordisk) for 24-48 hours; or the alpha-amylase encoded by the polynucleotide of the invention for a shorter time.

The alpha-amylase variant of the invention may also be used in baking processes. In one aspect the invention relates to the used of a variant of the invention for starch conversion, alcohol production, brewing, and baking.

The invention also relates to a process of producing maltose syrup comprising the steps of: 1) liquefying starch in the presence of an alpha-amylase; 2) dextrinization in the presence of a fungal alpha-amylase variant of the invention; and 3) recovery of the syrup; and optional purification of the syrup.

The alpha-amylase used for liquefaction in step 1) may be any alpha-amylase. Preferred alpha-amylase are *Bacillus* alpha-amylases, such as a Termamyl-like alpha-amylase, which including the *B. licheniformis* alpha-amylase (commercially available as Termamyl™ (Novo Nordisk)), the *B. amyloliquefaciens* alpha-amylase (sold as BAN (Novo Nordisk), the *B. stearothermophilus* alpha-amylase (sold as Termamyl™ 120 L type S), The alpha-amylases derived from a strain of the *Bacillus* sp. NCIB 12289, NCIB 12512, NCIB 12513 or DSM 9375, all of which are described in detail in WO 95/26397, and the alpha-amylase described by Tsukamoto et al., 1988, *Biochemical and Biophysical Research Communications*, 151: 25-31. Alpha-amylases within the definition of "Termamyl-like alpha-amylase" are defined in for instance WO 96/23874 (Novo Nordisk).

In another aspect the invention relates to a process of producing maltose comprising the steps of: 1) liquefying starch at a temperature of 140-160° C. at a pH of 4-6; 2) dextrinization at a temperature in the range from 60-95° C., in particular at 65-85° C., such as 70-80° C., at a pH 4-6 in the presence of a fungal alpha-amylase variant of the invention; and 3) recovery of the syrup; and optional purification of the syrup.

In an embodiment of the invention an effective amount of glucoamylase is added in step 2). The syrup will in this embodiment (including treatment with a glucoamylase) not be maltose syrup, but syrup with a different sugar profile. The glucoamylase may be an *Aspergillus* glucoamylase, in particular an *Aspergillus niger* glucoamylase.

Alternatively, the process comprising the steps of: 1) liquefying starch at a temperature of 95-110° C. at a pH of 4-6 in the presence of a Bacillus alpha-amylase; 2) liquefying at a temperature in the range from 70-95° C. at a pH 4-6 in the presence of an alpha-amylase encoded by a polynucleotide as defined in the first aspect of the invention, followed by recovery and/or optional purification of the product obtained.

Finally, some aspects of the invention relate to various detergent uses. One aspect relates to a detergent additive comprising an alpha-amylase encoded by a polynucleotide as defined in the first aspect, optionally in the form of a non-dusting granulate, stabilized liquid or protected enzyme. A preferred embodiment of this aspect relates to a detergent additive which contains 0.02-200 mg of enzyme protein/g of the additive. Another preferred embodiment relates to a detergent additive according to the previous aspect, which additionally comprises another enzyme such as a protease, a lipase, a peroxidase, another amylolytic enzyme and/or a cellulase. Another aspect relates to a detergent composition comprising an alpha-amylase encoded by a polynucleotide as defined in the first aspect, and a preferred embodiment of this aspect relates to a detergent composition which additionally comprises another enzyme such as a protease, a lipase, a peroxidase, another amylolytic enzyme and/or a cellulase. Still another aspect relates to a manual or automatic dishwashing detergent composition comprising an alpha-amylase variant encoded by a polynucleotide as defined in the first aspect. A preferred dishwashing detergent composition additionally comprises another enzyme such as a protease, a lipase, a peroxidase, another amylolytic enzyme and/or a cellulase. A final detergent related aspect is a manual or automatic laundry washing composition comprising an alpha-amylase variant encoded by a polynucleotide as defined in the first aspect; and a preferred laundry washing composition according additionally comprises another enzyme such as a protease, a lipase, a peroxidase, an amylolytic enzyme and/or a cellulase.

EXAMPLES

Example 1

Purification and characterization of the alpha-amylase from Rhizomucor pusillus NN046782.

This alpha-amylase denoted AM782 was purified from culture broth of thermophilic fungal strain NN046782, and it was found to be more stable than the BAN (*Bacillus amyloliquefaciens*) amylase at 60, 70, and 80° C., at pH=5.0, 6.0, and 7.0. The characteristics are summarized as following:

| | |
|---|---|
| Molecular weight (SDS) | ≈50 kDa (SDS-PAGE) |
| pI | pH 3.5 |
| Active pH range | pH 3-9 |
| Optimal pH | pH 4-5 |
| Active temperature range | 30-80° C. |
| Optimal Temperature | 70° C. |
| pH Stability | stable at pH = 5, 6, 7. |

Media for Fungal Growth

| YG: Yeast-glucose agar | |
|---|---|
| 5.0 g Difco powdered yeast extract | 10.0 g glucose |
| 20.0 g agar | 1000 ml tap water |
| Autoclave at 121° C. for 15-20 min. | |
| FG-4 Media 50 ml /flask: | |
| 30 g Soymeal, | 15 g Maltose |
| 5 g Peptone, | 1000 ml H$_2$O |
| 1 g olive oil (2 drops/flask) | |
| 50 ml in 500 ml Erlenmeyer flask with 2 baffles. | |
| Autoclave at 121° C. for 30 min. | |

The fungi were grown on YG agar plate (4.5 cm diam) for 3 days under 45° C. in the darkness and used for inoculating shake flask. The plates with fully grown cultures were stored at 4° C. before use.

For enzyme production, 4-6 agar plugs with fully grown fungal cultures on the above plates were used to inoculate one shake flask with FG-4 and grown under 45° C., 160 rpm for 72 hours, then harvested by centrifuged the culture broth at 8000 rpm and 4° C. for 30 minutes. The supernatant was collected and used for enzyme purification.

Chemicals and Regeants

BAN standard and Fungamyl™ 800L (Novozymes NS, Denmark) were used as benchmark. AZCL-amylose (Megazyme) was used for enzyme assay.

Other chemical and buffers include:
25 mM Tris-HCl, pH 7.0; 25 mM Tris-HCl; 1 M NaCl, pH7.0; 0.1 M Na$_3$PO$_4$/Citric Acid, pH 5.5; ammonium sulfate; 0.1 M NaAc, pH 5.0; 0.1 M MES, pH 6.0; 0.1 M Tris-HCl, pH 7.0

Buffer for pH profile: 100 mM succinic acid, 100 mM HEPES, 100 mM CHES, 100 mM CABS, 1 mM CaCl$_2$, 150 mM KCl, 0.01% Triton X-100 adjusted to pH-values 2.0, 3.0, 4.0, 5.0, 6.0, 7.0, 8.0, 9.0, 10.0 and 11.0 with HCl or NaOH Enzyme Activity Tests Microtiter plate assay:

The supernatants were tested for alpha-amylase activity by microtiter plate assay. A solution of 0.2% of the blue substrate AZCL-amylose (Megazyme) was suspended in a 0.1 M phosphate-citrate buffer (pH 5.5) or Tris-HCl buffer (pH 7) under stirring. The solution was distributed under stirring to a microtiter plate (200 microliters to each well), 20 microliters enzyme sample was added and the plates were incubated in an Eppendorf Thermomixer for 15-30 minutes at 50° C. and 650 rpm. Denatured enzyme sample was prepared at 100° C. boiling for 20 min and then used as blank controls. After incubation the colored solution was separated from the solid by centrifugation at 3000 rpm for 5 minutes at 4° C. Then 150 microliters of supernatant was transferred to a microtiter plate and the absorbance was measured in a BioRad Microplate Reader at 595 nm.

Eppendorf Tube Assay:

A solution of 0.2% of the blue substrate AZCL-amylose (Megazyme) was suspended in buffers at different pH-values under stirring. The solutions were distributed under stirring to 1.5 ml Eppendorf tubes (900 microliters to each), 100 micro-m enzyme sample is added to each tube and they were then incubated in a waterbath for 10-60 min. at 50° C. Denatured enzyme samples (prepared by 100° C. boiling for 20 min) were used as blank controls. After incubation the colored solution was separated from the solid by centrifugation at 5000 rpm for 10 minutes at 4° C. Then 200 microliters of supernatant was transferred into a microtiter plate and the absorbence was measured in a BioRad Microplate Reader at 595 nm.

Isoelectric Focusing

Isoelectric focusing was carried out in precast Apholine PAG plate pH 3.5-9.5 (Pharmacia, Sweden) according to the manufacturer's instructions. The samples were applied in triplicate and after electrophoresis the gel was divided into three. An overlay containing 1% agarose and 0.4% AZCL-amylose in buffer pH 5-7 was poured onto each part of the gel which was incubated at 45° C. for 12-16 hours. Enzyme activity and pI of enzyme protein was identified by blue zones.

SDS-PAGE

For checking of purifity and determing the molecular weight of purified amylase, 30 microliters of enzyme samples were applied to 12% SDS-poly acrylamide gel electrophoresis. The gel was run at 100 V for 1.5 hrs and stained with Coomassie blue.

Enzyme Purification 300 ml supernatant of the strain NN046782 was precipitated with ammonium sulfate (80% saturation) and redissolved in 20 ml 25 mM Tris-HCl buffer, pH7.0, then dialyzed against the same buffer and filtered through a 0.45 mm filter, the final volume was 200 ml. The solution was applied to a 35 ml Source 15Q column (Phamacia) equilibrated in 25 mM Tris-HCl buffer, pH 7.0, and the proteins was eluted with a linear NaCl gradient (0-0.3 M). Fractions from the column were analyzed for amylase activity on AZCL-amylose at pH 5.5. Fractions with amylase activity were pooled. Then the pooled solution was ultrafiltrated, the concentrated solution was applied to a 180 ml Superdex75 column equilibrated with 25 mM Tris-HCl, pH7.0, the proteins was eluted with the same buffer. Amylase containing fractions were analyzed by SDS-PAGE and pure fractions were pooled.

Enzyme Characterization pH profile:

20 microliters enzyme sample and 200 microliters 0.2% AZCL-amylose in the following buffer system (100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0 and 11.0 with HCl or NaOH) with different pH were mixed in an Microtiter plate and placed on ice before reaction. The assay was initiated by transferring the Microtiter plate to an Eppendorf thermomixer, which was set to the assay temperature 50° C. The plate was incubated for 20 minutes on the Eppendorf thermomixer at 650 rpm shaking rate. The incubation was stopped by transferring the plate back to the ice bath. Then the plate was centrifuged in an ice-cold centrifuge for a few minutes and 150 microliters supernatant was transferred to a new microtiter plate. The absorbance, $OD_{595}$, was read as a measure of amylase activity. All reactions were done in triplicate, and a buffer blind was included in the assay (instead of enzyme). BAN and Fungamyl™ commercial enzymes were used as positive controls. The results are shown in FIG. 1.

Figure 2:
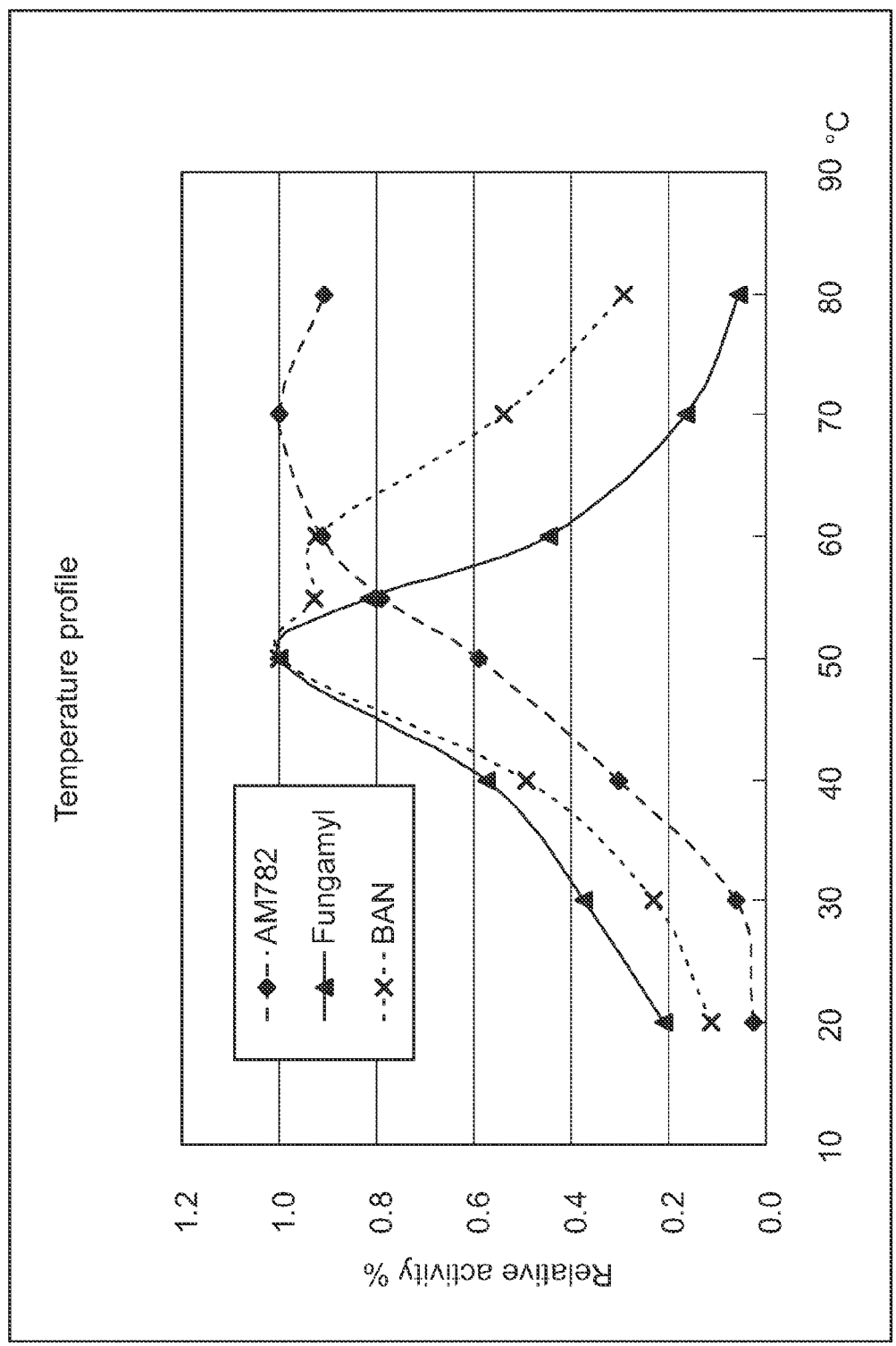
FIG. 2 shows the temperature profiles of the amylases AM782, FUNGAMYL™ and BAN.
Figures 1, 3:
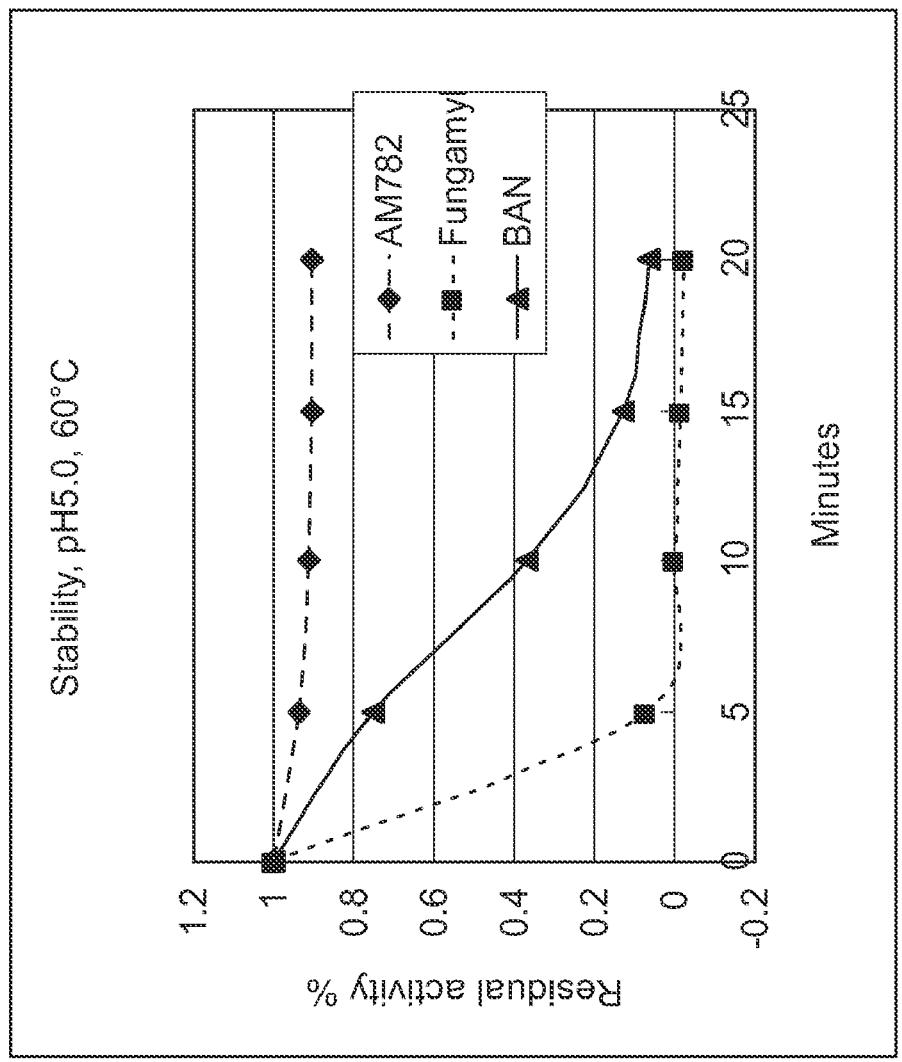
Figures 2, 3:
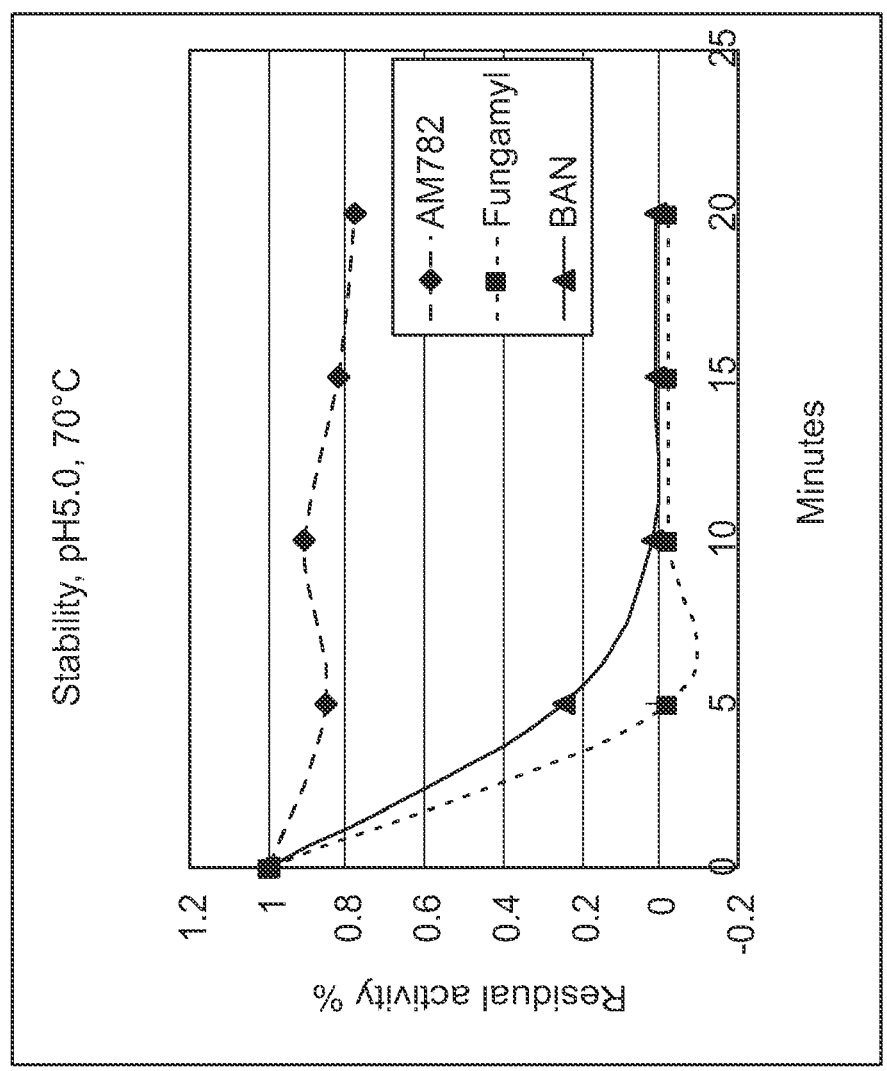
Figure 3:
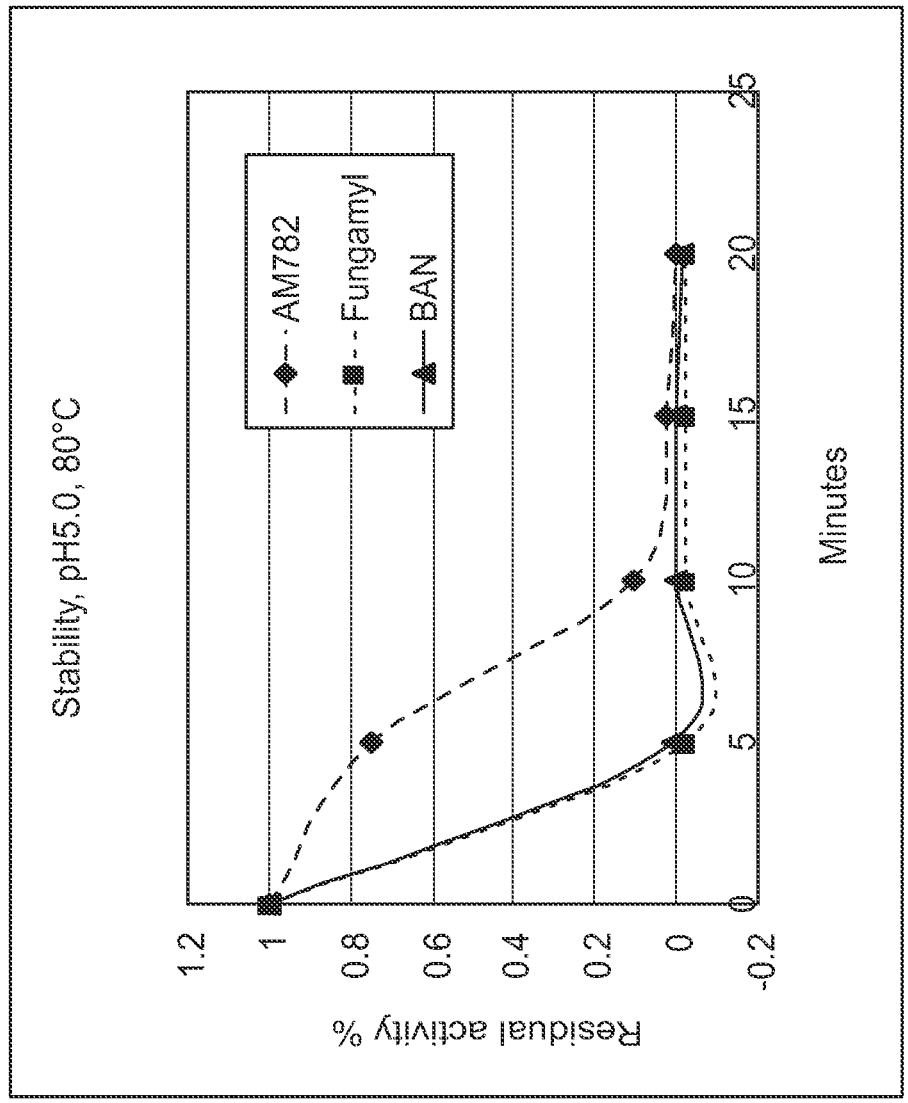
Figures 1, 4:
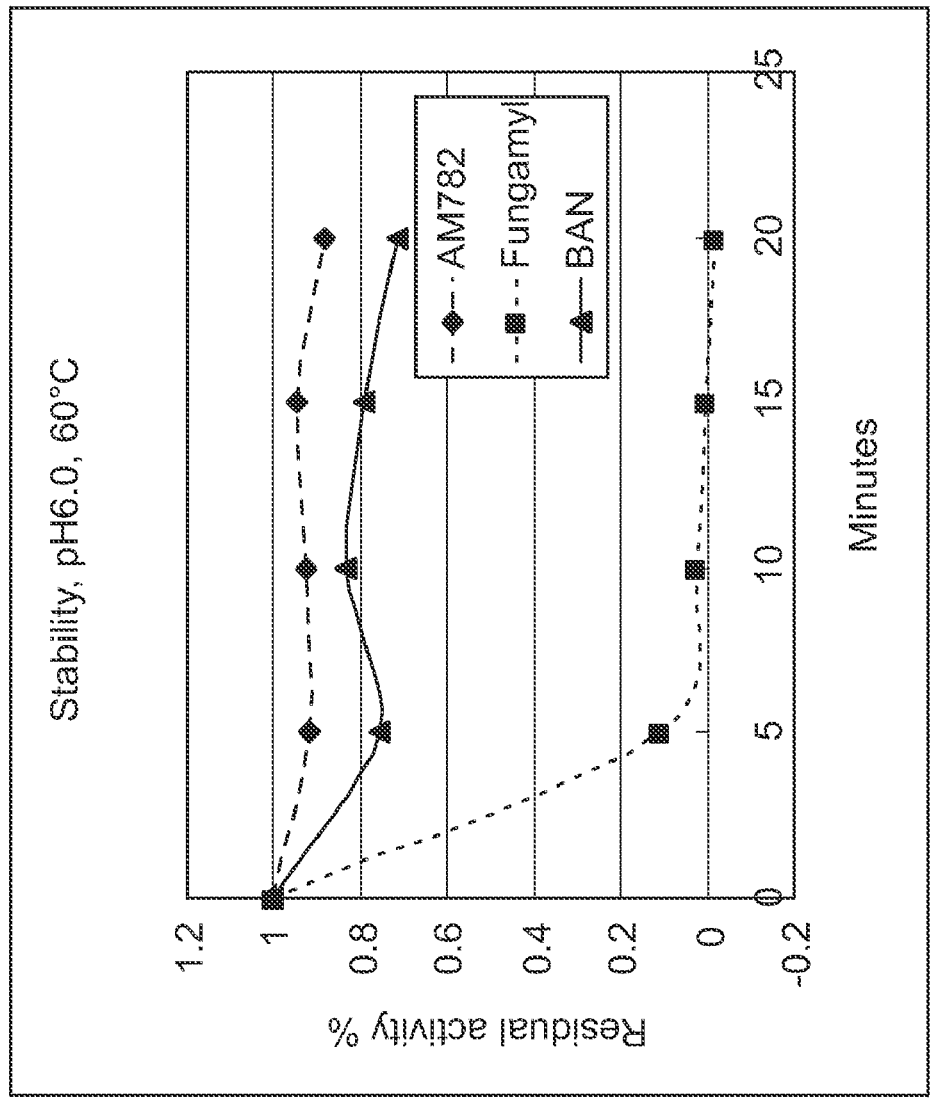
Figures 2, 4:
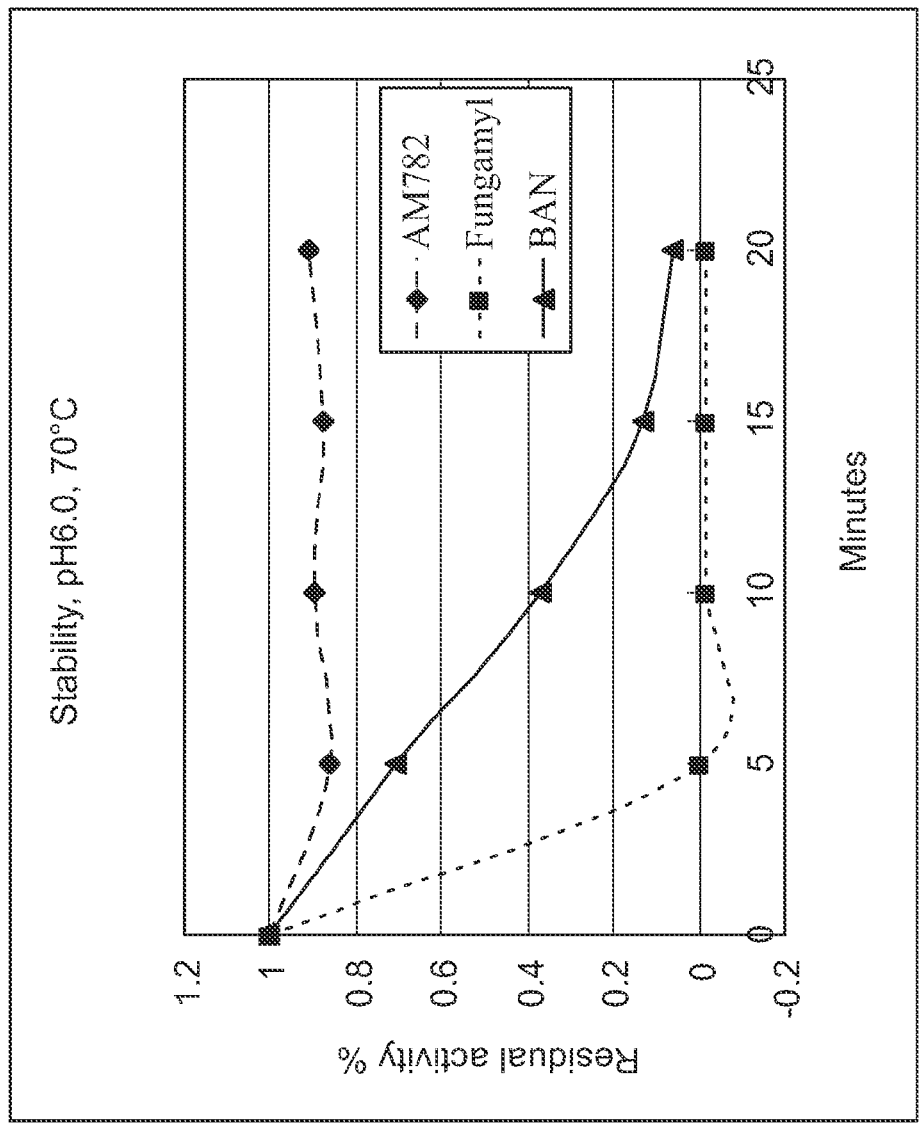
Figures 3, 4:
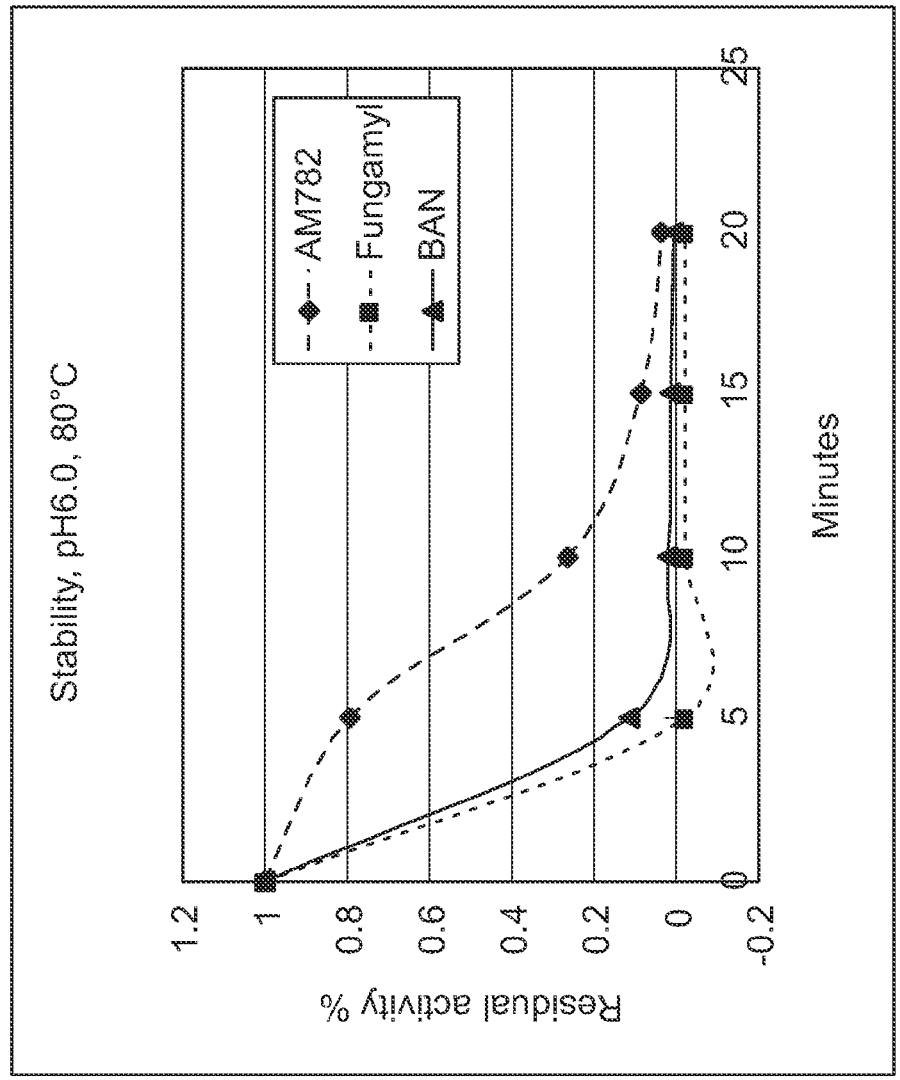
Figures 1, 5:
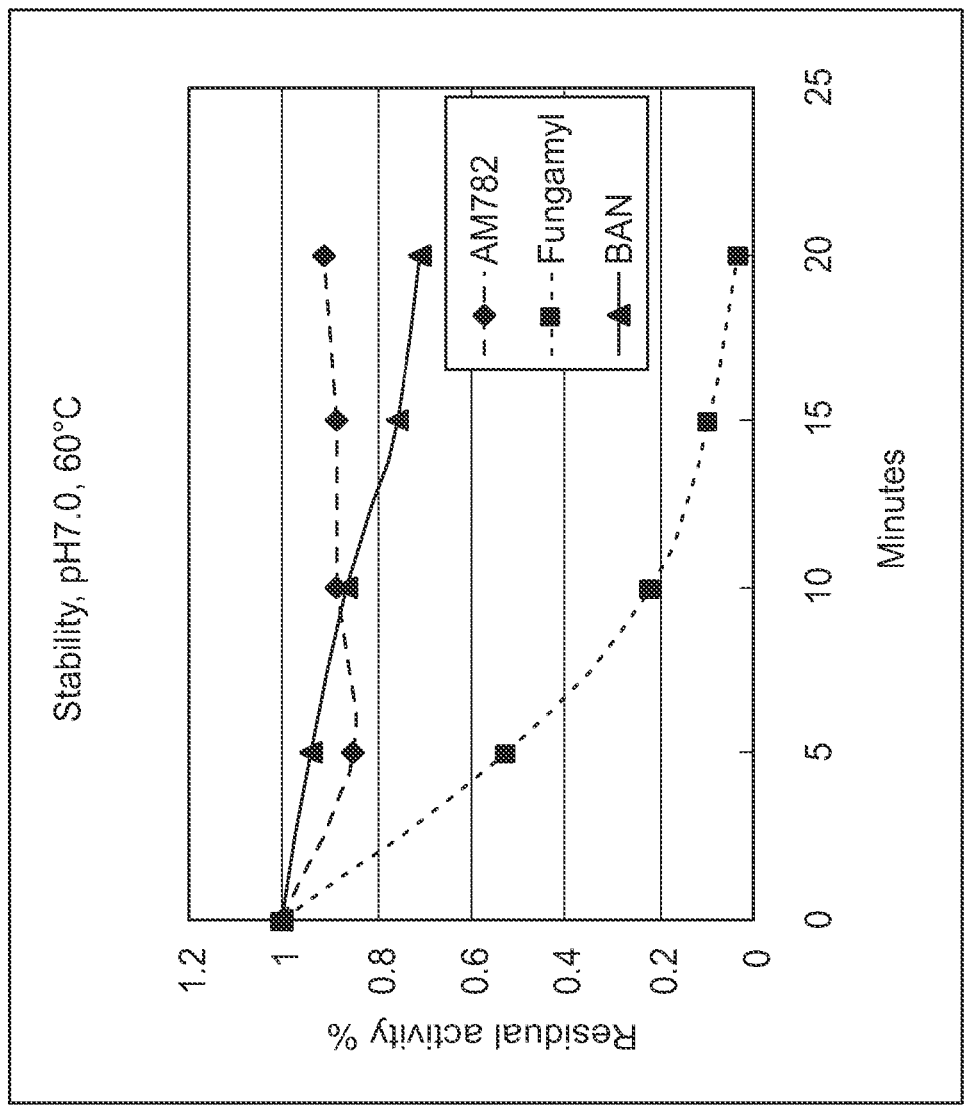
Figures 2, 5:
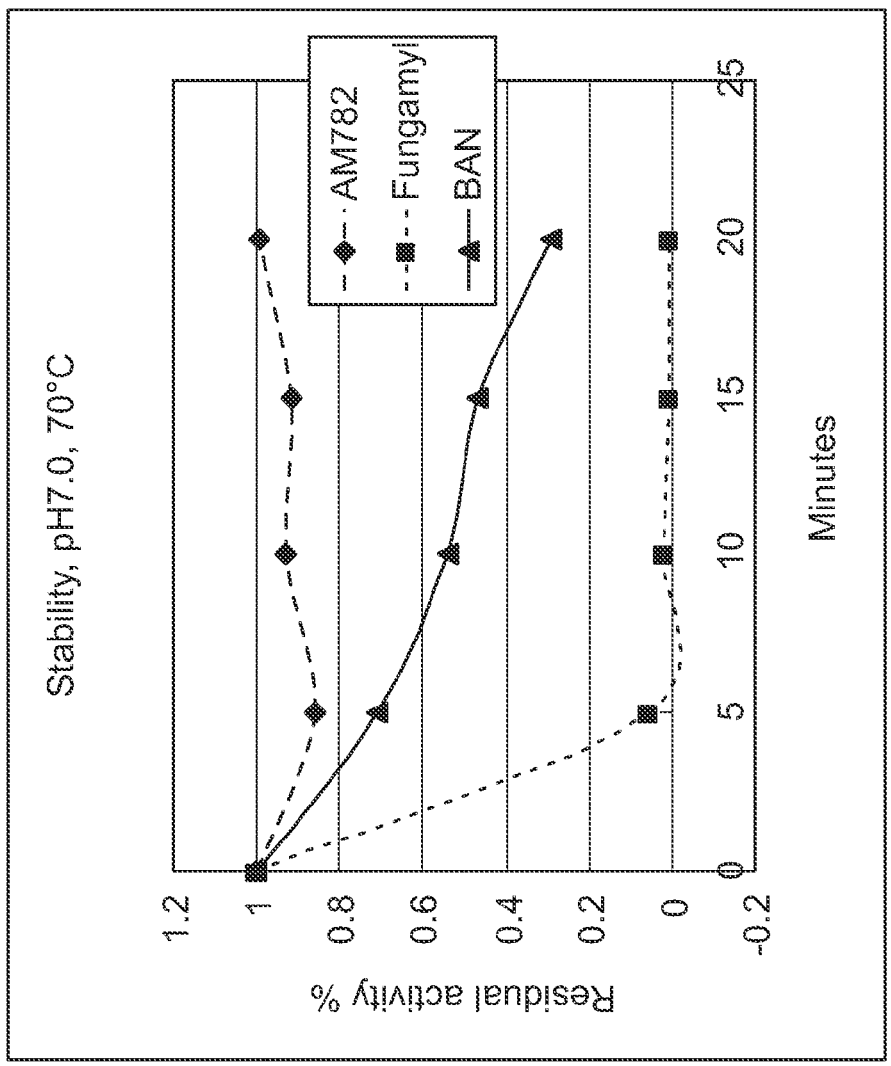
Figures 3, 5:
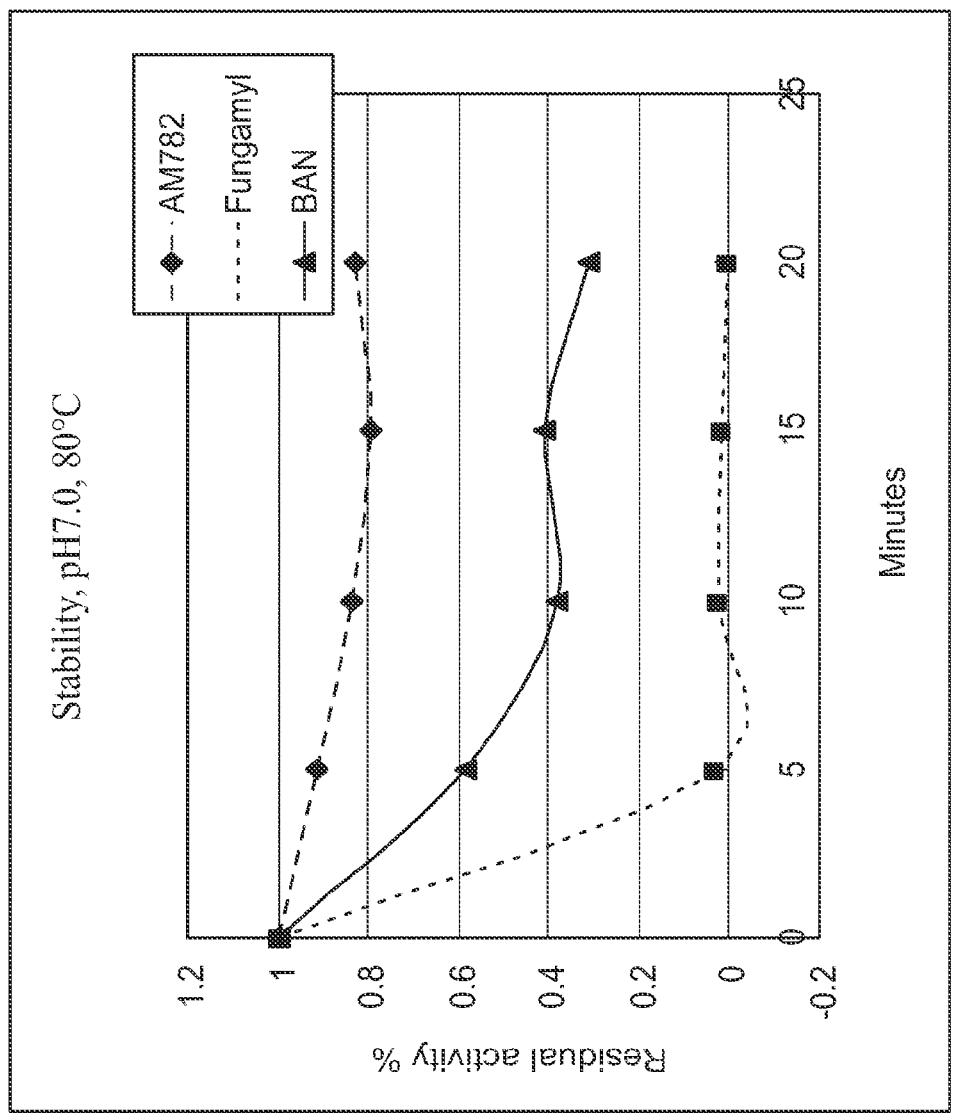

Temperature Profile:

Eppendorf tubes with 200 microliters 0.2% AZCL-amylose in 0.1 M $Na_3PO_4$/Citric acid buffer pH 5.5 were pre-incubated at 20, 30, 40, 50, 55, 60, 70, 80° C. The assay was initiated by mixing 20 microliters enzyme sample with the buffer. The tubes were incubated for 10 minutes on the Eppendorf thermomixer at its highest shaking rate (1400 rpm). The incubation was stopped by transferring the tube to the ice bath. Then the tubes were centrifuged in an icecold centrifuge for a few minutes and 150 microliters supernatant was transferred to a microtiter plate. $OD_{595}$ was read as a measure of amylase activity. All reaction was done with triplicate and a buffer blind was included in the assay (instead of enzyme). BAN and Fungamyl™ were used as control. The results are shown in FIG. 2.

pH and Themperature Stability:

80 microliters enzyme sample (diluted with 0.1 M NaAc pH 5.0, 0.1 M MES pH 6.0, 0.1 M Tris-HCl pH7.0 respectively) in an Eppendorf tube was incubated for 5, 10, 15 and 20 minutes on the Eppendorf Thermomixer at 60, 70, 80° C. and 300 rpm shaking. The incubation was stopped by transferring the tube back to the ice bath. Un-incubated sample was used as control. The 20 microliters of the above incubated sample was transferred into a new microtiter plate and 200 microliters 0.2% AZCL-amylose in 0.1 M $Na_3PO_4$/Citric buffer pH 5.5 was added. The assay was initiated by transferring the Microtiter plate to an Eppendorf thermomixer, which was set to the assay temperature 50° C. The plate was incubated for 30 minutes on the Eppendorf thermomixer at 650 rpm shaking rate. The incubation was stopped by transferring the plate back to the ice bath. Then the plate was centrifuged in an ice-cold centrifuge for a few minutes and 150 microliters supernatant was transferred to a new microtiter plate. $OD_{595}$ was read as a measure of amylase activity. All reaction was done with duplicate and a buffer blind was included in the assay (instead of enzyme). BAN and Fungamyl™ were used as control. The results are shown in FIGS. 3-5.

Side Activity Assay:

The purified amylase was tested in follow substrates at pH 7.0: AZCL-galactomannan, AZCL-beta-glucan, AZCL-dextran, AZCL-xyloglucan, AZCL-potato galactan, AZCL-arabinan, AZCL-pullulan, AZCL-xylan, AZCL-he-cellulose, AZCL-casein. No side-activity was detected in any of the subtrates.

The purity of purified amylase was checked in 12% SDS-page, the molecular weight of the enzyme is around 50 KDa as seen on SDS-PAGE, the pl of AM782 is around pH3.5 as determined by IEF.

Example 2

Cloning of the gene encoding the AM782 alpha-amylase of Rhizomucor pusillus NN046782.

Fungal Strain and Its Growth

Rhizomucor pusillus NN046782 was grown at 45° C., 165 rpm for 48 hours in FG4 medium with 2% starch. The mycelium was harvested by centrifugation at 7000 rpm for 30 minutes. The harvested mycelium was stored at −80° C. before use for RNA extraction.

Extraction of Total RNA

Total RNA was extracted from 100 mg mycelium using the RNeasy Mini Kit (Qiagen).

Specific Primers

It was found that the amylase AM782 from Rhizomucor pusillus NN046782 had the same N-terminal sequence as an amylase encoding gene which had been identified and sequenced by us at in an earlier project from another Rhizomucor pusillus strain NN101459. Thus two specific primers were designed from the previously determined DNA sequence, and these were used for the cloning of amylase from NN046782. Primer AM298-CDSF (SEQ ID NO: 1): 5'-tat cat gaa att cag cat Primer AM298-CDSR (SEQ ID NO: 2): 5'-agt tca aaa tgg aca aag t The following PCR reaction system and conditions were used:

| | |
|---|---|
| Pfu DNA polymerase 10 x PCR buffer with $MgSO_4$ | 5 microliters |
| 10 mM dNTP mix | 1 microliter |
| Primer AM298-CDSF (10 micro-M) | 1 microliter |
| Primer AM298-CDSR (10 micro-M) | 1 microliter |
| pfu DNA polymerase (3 u/microliter) | 0.5 microliter |
| cDNA synthesis reaction (template) | 2 microliters |
| Add autoclaved, distilled water to | 50 microliters |

Conditions:

| | | |
|---|---|---|
| 95° C. | 3 min | |
| 95° C. | 30 sec | |
| 45 or 50 or 53° C. | 30 sec | 40 cycles |
| 72° C. | 3 min | |
| 72° C. | 7 min | |

The PCR product was viewed on agarose gel and a specific band was identified and purified. Thus 0.3 microliter of this PCR product was used as template for second round PCR at the following conditions.

| | |
|---|---|
| Pfu DNA polymerase 10 x PCR buffer with $MgSO_4$ | 5 microliters |
| 10 mM dNTP mix | 1 microliter |
| Primer AM298-CDSF (10 micro-M) | 1 microliter |
| Primer AM298-CDSR (10 micro-M) | 1 microliter |
| pfu DNA polymerase (3 u/microliter) | 0.5 microliter |
| cDNA synthesis reaction | 0.3 microliter |
| Add autoclaved, distilled water to | 50 microliters |

Conditions:

| | | |
|---|---|---|
| 95° C. | 3 min | |
| 95° C. | 30 sec | |
| 55° C. | 30 sec | 40 cycles |
| 72° C. | 3 min | |
| 72° C. | 7 min | |

A specific band with the size of about 1.5 kb was the result of this amplification. A polyA tail was added using Taq DNA polymerase (PCR product 20 microliters, 10× buffer 2 microliters, Mg2+1 microliter, dATP (10 mM) 0.5 microliter, Taq polymerase (5 unit/microliter) 0.3 microliter) and incubation at 72° C. for 30 min. The dA-tailed fragment was recovered from the gel with GFX Kit and redissolve into 30 microliters water. Then the purified fragment was ligated into the pGEM-T Vector (by mixing 2× buffer 10 microliters, T-vector (50 ng/l) 1 microliter, T4 ligase (3 unit/l) 1 microliter and purified PCR product 8 microliters; then let it stay overnight at 4° C.), and transformed it into the competent cells (transformation condition: 1 microliter ligation solution and 40 microliters DH10B competent cell in 0.1 cm curvette, 1.8 KV). 8 positive clones were screened by colony PCR.
Colony PCR system:

| | |
|---|---|
| 10 x PCR buffer | 5 microliters |
| 25 mM MgCl$_2$ | 3 microliters |
| 10 mM dNTP mix | 1 microliter |
| AM298-CDSF | 1 microliter |
| AM298-CDSR | 1 microliter |
| pfu polymerase | 1 microliter |
| Add autoclaved, distilled water to | 50 microliters |

A white colony was transferred directly into PCR mixture where it served as the template. The PCR conditions were as follows:

| | | |
|---|---|---|
| 94° C. | 3 min | |
| 94° C. | 30 sec | |
| 55° C. | 30 sec | 30 cycles |
| 72° C. | 1 min | |
| 72° C. | 10 min | |

After PCR reaction, 10 microliters PCR products were loaded into 1% agarose in 0.5× TBE buffer and run through the gel under 90 V for 1 hour and then visulized under UV, all colonies gave positive result.

Then plasmid was extracted from 3 of these 8 clones with Wizards Plus Minipreps DNA Purification System (Promega). The plasmids were sequenced using the ET terminator kit (Amersham) with the two primers AM298-CDSF and AM298-CDFR, and the 3 clones turned out to be identical, the full-length sequence is shown in SEQ ID NO: 3.

A plasmid comprising a DNA sequence encoding the alpha-amylase AM782 has been transformed into a strain of the Escherichia coli DH10B which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on 29 Nov. 2002 under the deposition number DSM 15334. The deposit was made by Novozymes NS. It is contemplated that the DNA sequence of this plasmid comprises the DNA sequence of SEQ ID NO: 3.

Further sequence analysis of the cDNA clone showed that the sequence contains a coding region of 1413 nucleotides. The translation product of the coding region is a peptide of 471 amino acids. The deduced amino acid sequence encoded by this gene, with a signal peptide (from aa 1-21) and a mature peptide (from aa 22-471) is shown in SEQ ID NO: 4.

Example 3

Subcloning and heterologous expression of AM782 amylase.
Strains and Plasmids

Figure 6:
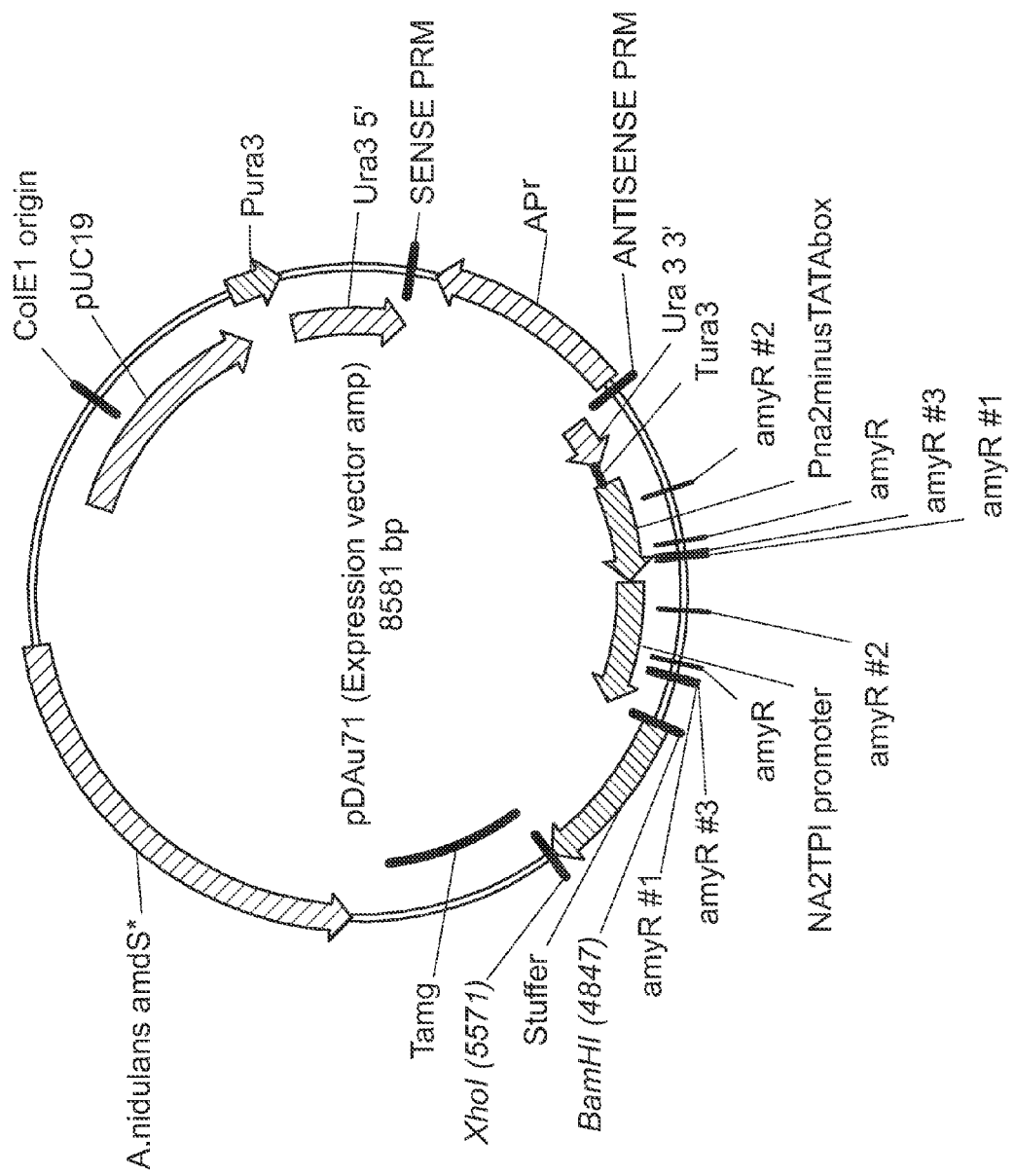
FIG. 6 shows the *Aspergillus* expression vector pDAu71.

The *A. oryzae* strain BECh2, used as expression host has the following genotype: amy, alp⁻, Npl⁻, CPA⁻, KA⁻ *E. coli* DHSalpha (Invitrogen™) was used as cloning host in construction of the expression vector. The expression plasmid pDAu71 (FIG. 6) containing the *A. nidulans* amdS gene as selection marker in *Aspergillus* and the Ampicillin resistance gene for selection in *E. coli*, two copies of the *A. niger* NA2 promoter (neutral amylase) with 3 extra amyR-sites +the 5' untranslated part of the *A. nidulans* TPI promoter for heterologous expression and the *A. niger* AMG terminator was used.
PCR Amplification:

| | |
|---|---|
| 10 x PCR buffer (incl. MgCl$_2$) | 5 microliters |
| 2.5 mM dNTP mix | 5 microliters |
| 168/R.p. amy3-forw (10 μM) | 5 microliters |
| 169/R.p. amy4-rev (10 μM) | 5 microliters |
| Expand High Fidelity polymerase (Roche) | 0.5 microliter |
| Template DNA | 1 microliter |
| Add autoclaved, distilled water to | 50 microliters |

Conditions

| | | |
|---|---|---|
| 95° C. | 1 min | 1 cycle |
| 94° C. | 30 sec | |
| 60° C. | 30 sec | 20 cycles |
| 72° C. | 1.30 min | |
| 72° C. | 2 min | 1 cycle |

Construction of plasmid pPFJo143 (FIG. 13): A DNA fragment containing the AM782 gene was PCR amplified from a plasmid containing the full length cDNA with primers designed from the full sequence:
Primer 168/R.p. amy3-forw (SEQ ID NO: 5): gaagatctaccatgaaattcagcatctctctc
Primer 169/R.p. amy4-rev (SEQ ID NO: 6): ccgctcgagttaagcagaggtgaagatagc The primers have cloning restriction sites BglII-Xhol, respectively, in the ends. A pool of PCR product from individual PCR reactions was used for the cloning. The PCR product was digested with BglII and Xhol and cloned into pDAu71, digested with BamHl and Xhol. The PCR product was sequenced and verified to be identical to the original sequence.

Transformation of BECh2 was performed by a method involving protoplast formation and transformation of these. Suitable procedures for *Aspergillus* transformation are described in EP 0238023 and Yelton et al., 1984, *Proceedings of the National Academy of Sciences USA* 81: 1470-1474. Transformants were isolated and grown in small Nunc-containers in 10 ml of YPM (1% yeast extract, 2% Bacto peptone, and 2% maltose) for 3 days at 30° C. (rotated).

SDS-page gel electrophoresis: 10 microliters supernatant samples from the above described 10 ml cultures were subjected to SDS-gel electrophoresis. Gels were stained with SYPRO Orange Protein Gel Stain (Molecular Probes).

Alpha-amylase was assayed by PNP as follows. A working solution was made: 5 ml alpha-glucosidase solution +1 ml substrate solution (PNP-substrate). TermamylTM was used as standard (concentrations from 0-100 NU/ml). Buffer for dilution: 50 mM acetic acid, boric acid and phosphorous acid and 0.1 mM $CaCl_2$ +0.25% BRIJ35. 20 microliters supernatant in a microtiter plate was incubated for 2 mins. 200 microliters working solution was added. Kinetics at 405 nm over 3 min.

Figure 7:
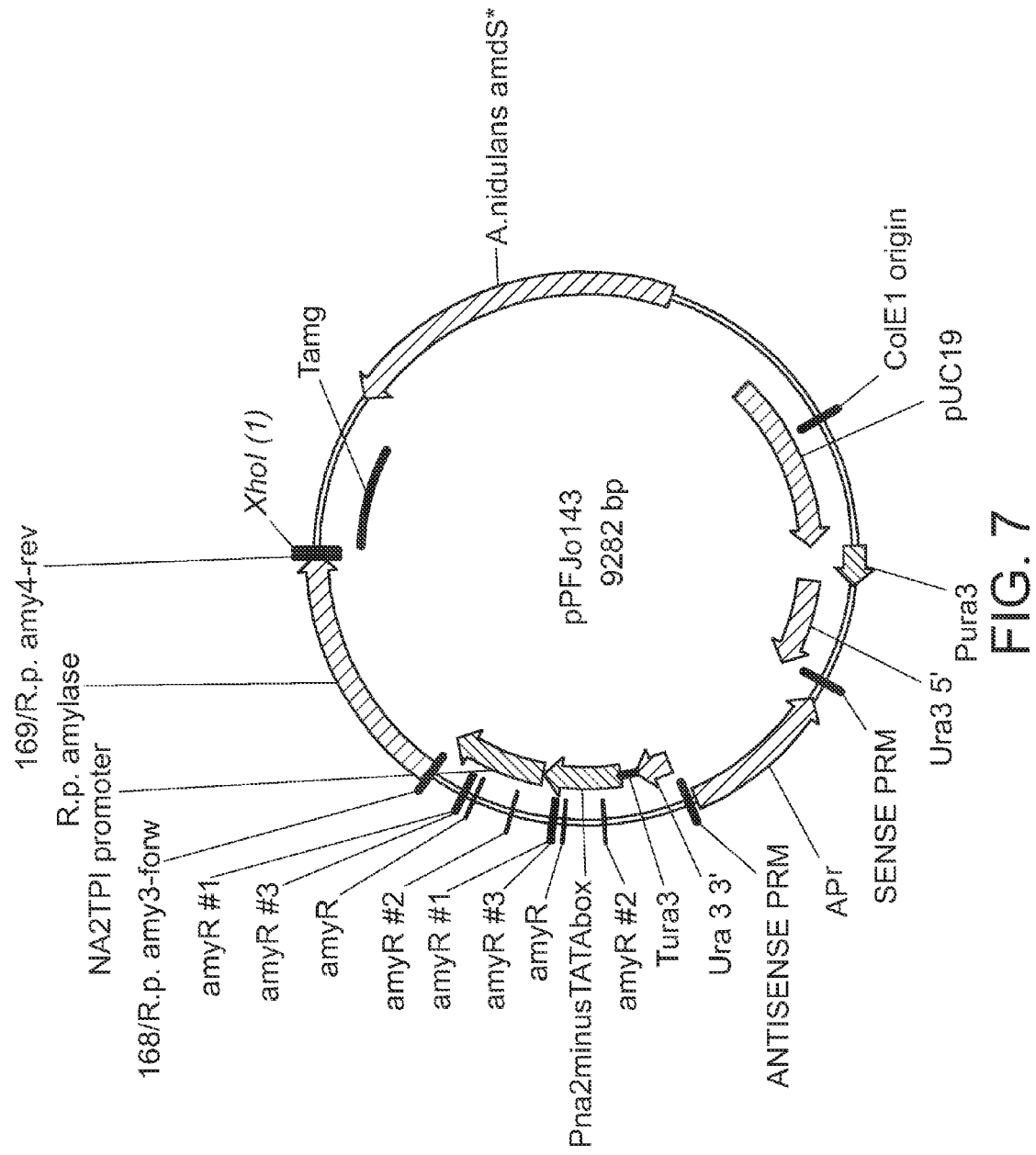
FIG. 7 shows the amylase expression vector pPFJo143.

The PCR amplified ORF was cloned into the expression vector pDAu71, resulting in pPFJo143 as described in Materials and Methods (FIG. 7). The plasmid was transformed into BECh2 (*A. oryzae*). 10 transformants were isolated, grown in YPM for 3 days and supernatants run on an SDS-PAGE. This showed varying expression levels ranging from very little to quite good expression. The molecular weight is around 50 kDa, in accordance with what was found for the wild type enzyme. Transformant BECh2/pPFJo143-9 was chosen to ferment for a small scale purification of the amylase. An alpha-amylase assay was performed according to Materials and Methods (Table 1). It was performed with TermamylTM as a standard—and the units are NU/ml—which means that it only gives us relative numbers, but we could see that there was a good correlation between activity and amount of protein.

TABLE 1

Supernatants from fermentation of the 10 transformants 143-1 to 143-10 were subjected to an alpha-amylase assay using a PNP-substrate. The numbers are relative.

| | Transf. | | | | | | | | | |
|---|---|---|---|---|---|---|---|---|---|---|
| | 1 | 2 | 3 | 4 | 5 | 6 | 7 | 8 | 9 | 10 |
| NU/ml | 155 | 192 | 241 | 195 | 166 | 240 | 107 | 212 | 342 | 205 |

Example 4

Investigation of the sugar profile of maltodextrin hydrolysis by the alpha-amylase AM782

Apparatus

Thermostated water bath Heto lab equipment DT1; pH-meter (Mettler MP220); HPLC Waters system (NP TSCN-QI-2411); Electronic pipette; Spectrophotometer UV-1601; Balance (Mettler AG 204); Refractometer.

Glassware 250 ml flask with lid; heavy rings for flask; 500 ml volumetric flask; 500 ml beaker; 10 ml glass tubes.

Enzymes

AM 782 alpha-amylase at 0.225 FNU/ml, and as control a commercially available fungal amylase Fungamyl™ 800L (Novozymes NS, Denmark; AFN-000515) at 0.135FNU/g.ds.

Substrate

DE 11 maltodextrin FFS-99039

Protocol

Two water baths were set up with a temperature of 55° C. and 70° C. respectively. 53 g of maltodextrin was slowly added into 397 g boiling Milli-Q water in a glass beaker and stirred with an electronic stirrer simultaneously, until all the maltodextrin was dissolved in the water. The weight of the maltodextrin solution was noted, and more boiling water was added up to 450 g. The maltodextrin solution was transferred into the water bath and cooled down to hydrolysis temperature. Then the maltodextrin solution was divided into two equal portions: one portion was adjusted to pH 5.0 with 1 N HCl; the rest was kept at its natural pH (5.5). The substrate concentration was checked by refractometer (DS about 10%).

The maltodextrin solutions were transferred into four 250 ml flasks with lids: flask #1 with 90 g pH 5.5 solution; flasks #2 & #3 with 90 g pH 5.0 solution; flask #4 with 95 g pH 5.5 solution. The flasks were kept in the water baths at hydrolysis temperature, flasks #1-3 at 70° C., and flask #4 at 55° C.

10 ml diluted AM782 enzyme (6 ml AM782 sample with 4 ml Milli-Q water) was added to each of the flasks #1-3 containing 90 g solution, and 5 ml diluted Fungamyl™ (0.04 g Fungamyl in 100 ml Milli-Q water) was added to flask #4 containing 95 g solution. In this way, the AM782 and Fungamyl™ was dosaged at the same activity level i.e., 0.135 FNU/g.ds.

The pH of each flask was checked and the DS of each flask was measured by sampling at T=0 hours. Thereafter 4 ml samples were taken from each shake flask at T=3, 6, 9, 21, 24, 28, 45, and 48 hours after incubation in the water baths.

Figure 8:
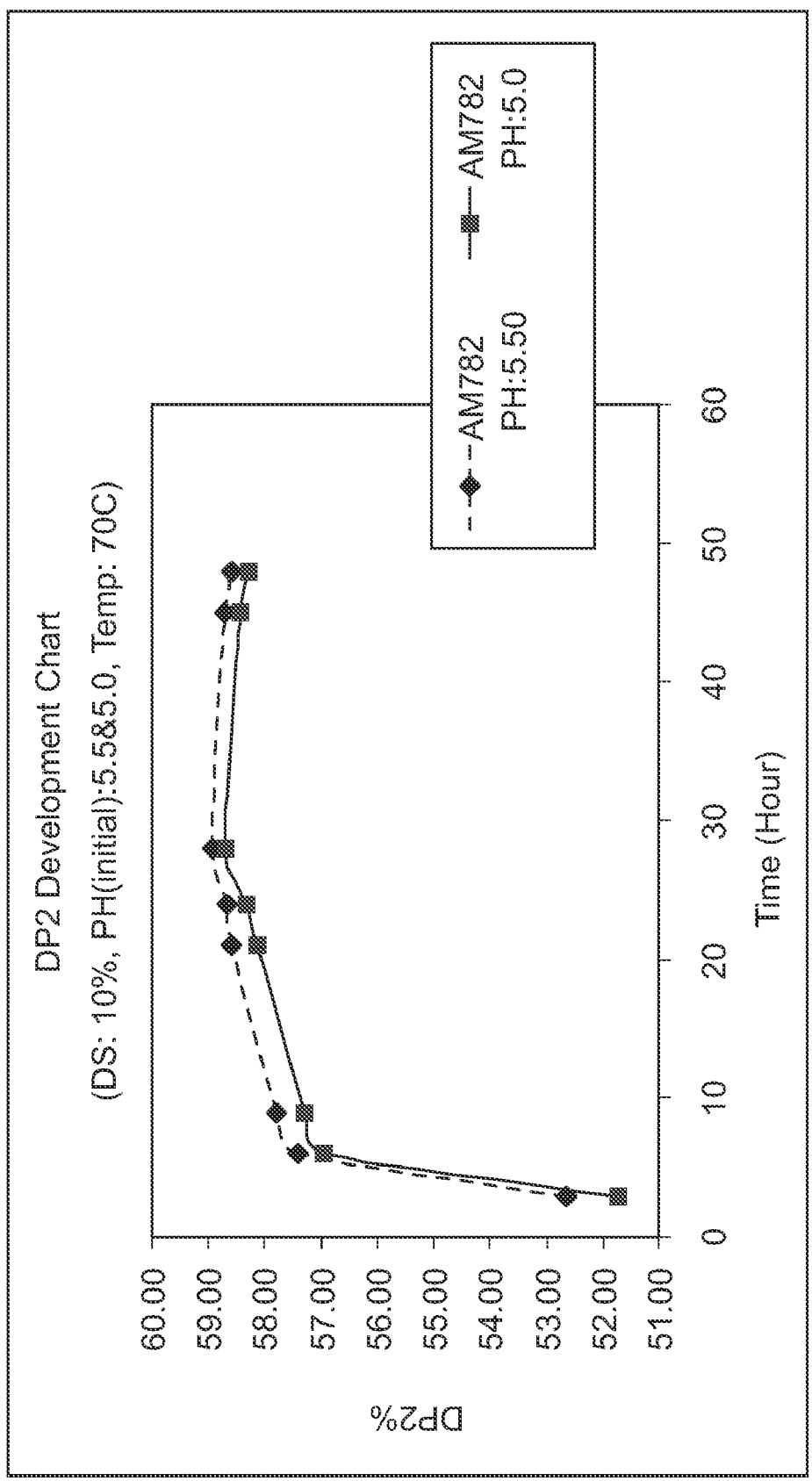
FIG. 8 shows results of the sugar profile of maltodextrin hydrolysis by the alpha-amylase AM782.

The enzymes in the hydrolysis samples were inactivated immediately after sampling by boiling the samples for 15 minutes, and then cooling them down to room temperature for HPLC analysis. After cooling, pH and DS was measured for each sample in order to determine sample dilution, and then the sample was diluted with Milli-Q water to a concentration of DS=5%. The samples were mixed with mixed bed ion-exchange resin (Bio-Rad AG 501/X8 (D)) and left to stand for 20 minutes, this removed ash and soluble N from the samples. The samples were then filtered through a 0.2 micro-m filter (Sartorius MINISART™ NML 0.2 micron) and the filtered samples were collected in HPLC bottles and analyzed by HPLC. The results are given in tables 2-4 below, and in FIG. 8.

TABLE 2

Flask #1 with AM782 (0.135 FAU/g.ds.) at 70° C., and initial pH 5.5.

| Hours | PH | % DS | % DP1 | % DP2 | % DP3 | % DP4 |
|---|---|---|---|---|---|---|
| 3 | 6.05 | | 7.59 | 52.63 | 16.54 | 23.25 |
| 6 | 6.03 | | 13.74 | 57.39 | 8.61 | 20.26 |
| 9 | 6.02 | | 16.46 | 57.78 | 6.12 | 19.64 |
| 21 | 5.88 | | 19.08 | 58.57 | 4.37 | 17.98 |
| 24 | 5.83 | | 18.78 | 58.65 | 4.34 | 18.22 |
| 28 | 5.82 | | 18.47 | 58.92 | 4.25 | 18.37 |
| 45 | 5.61 | | 19.04 | 58.71 | 4.07 | 18.18 |
| 48 | 5.58 | 12.3 | 18.72 | 58.59 | 4.28 | 18.42 |

TABLE 3

Flasks #2 & #3 with AM782 (0.135 FAU/g.ds.) at 70° C. and initial pH 5.0.

| Hours | PH | % DS | % DP1 | % DP2 | % DP3 | % DP4 |
|---|---|---|---|---|---|---|
| 3 | 5.89 | | 7.34 | 51.74 | 16.56 | 24.37 |
| 6 | 5.88 | | 13.66 | 56.96 | 8.61 | 20.78 |
| 9 | 5.87 | | 16.13 | 57.29 | 6.53 | 20.05 |
| 21 | 5.75 | | 18.13 | 58.12 | 4.87 | 18.88 |
| 24 | 5.72 | | 17.99 | 58.33 | 5.02 | 18.68 |
| 28 | 5.74 | | 17.54 | 58.69 | 4.83 | 18.95 |
| 45 | 5.53 | | 17.79 | 58.45 | 4.87 | 18.90 |
| 48 | 5.52 | 11.9 | 17.85 | 58.29 | 4.91 | 18.95 |

TABLE 4

Flask #4 with Fungamyl™ 800L (0.135 FAU/g.ds.) at 55° C. and initial pH 5.5.

| Hours | PH | % DS | % DP1 | % DP2 | % DP3 | % DP4 |
|---|---|---|---|---|---|---|
| 20 | 6.12 | 10.8 | 1.41 | 45.27 | 28.19 | 25.13 |
| 24 | 6.05 | 10.9 | 1.73 | 45.39 | 27.67 | 25.21 |

This experiment showed that the amylase AM782 can work at a very high temperature, at least up to 70° C. The amylase AM782 has a very fast reaction speed; when compared at the same dosage with Fungamyl™ 800 L, the amylase AM782 can achieve in about 3 hours, what takes Fungamyl™ 24 to 48 hours. Furthermore, the amylase AM782 can degrade DP3 into DP2 and DP1, so it gives a higher DP1 result.

The invention claimed is:

1. An isolated polypeptide having alpha-amylase activity, selected from the group consisting of:
    (a) a polypeptide with at least 90% sequence identity with the sequence of amino acids 1 to 450 of SEQ ID NO: 4;
    (b) a polypeptide encoded by a polynucleotide with at least 90% sequence identity with the sequence of nucleotides 68 to 1417 of SEQ ID NO: 3;
    (c) a polypeptide with at least 90% sequence identity to the polypeptide encoded by the amylase encoding part of the polynucleotide inserted into a plasmid present in the E. coli host deposited under the Budapest Treaty with DSMZ under accession number DSM 15334; and
    (d) a fragment of the sequence of amino acids 1 to 450 of SEQ ID NO: 4 that has alpha-amylase activity.

2. The polypeptide of claim 1, which at least 90% sequence identity with the sequence of amino acids 1 to 450 of SEQ ID NO: 4.

3. The polypeptide of claim 1, which at least 95% sequence identity with the sequence of amino acids 1 to 450 of SEQ ID NO: 4.

4. The polypeptide of claim 1, which at least 97% sequence identity with the sequence of amino acids 1 to 450 of SEQ ID NO: 4.

5. The polypeptide of claim 1, which comprises the sequence of amino acids 1 to 450 of SEQ ID NO: 4.

6. The polypeptide of claim 1, which consists of the sequence of amino acids 1 to 450 of SEQ ID NO: 4.

7. The polypeptide of claim 1, which is encoded by a polynucleotide with at least 90% sequence identity with the sequence of nucleotides 68 to 1417 of SEQ ID NO: 3.

8. The polypeptide of claim 1, which is encoded by a polynucleotide with at least 95% sequence identity with the sequence of nucleotides 68 to 1417 of SEQ ID NO: 3.

9. The polypeptide of claim 1, which is encoded by a polynucleotide with at least 97% sequence identity with the sequence of nucleotides 68 to 1417 of SEQ ID NO: 3.

10. The polypeptide of claim 1, which has at least 90% sequence identity to the polypeptide encoded by the amylase encoding part of the polynucleotide inserted into a plasmid present in the *E. coli* host deposited under the Budapest Treaty with DSMZ under accession number DSM 15334.

11. The polypeptide of claim 1, which has at least 95% sequence identity to the polypeptide encoded by the amylase encoding part of the polynucleotide inserted into a plasmid present in the *E. coli* host deposited under the Budapest Treaty with DSMZ under accession number DSM 15334.

12. The polypeptide of claim 1, which has at least 97% sequence identity to the polypeptide encoded by the amylase encoding part of the polynucleotide inserted into a plasmid present in the *E. coli* host deposited under the Budapest Treaty with DSMZ under accession number DSM 15334.

13. The polypeptide of claim 1, which comprises the polypeptide encoded by the amylase encoding part of the polynucleotide inserted into a plasmid present in the *E. coli* host deposited under the Budapest Treaty with DSMZ under accession number DSM 15334.

14. The polypeptide of claim 1, which consists of the polypeptide encoded by the amylase encoding part of the polynucleotide inserted into a plasmid present in the *E. coli* host deposited under the Budapest Treaty with DSMZ under accession number DSM 15334.

15. The polypeptide of claim 1, which is a fragment of the sequence of amino acids 1 to 450 of SEQ ID NO: 4 that has alpha-amylase activity.

16. A process for producing a hydrolyzed starch, comprising treating a starch with a polypeptide of claim 1.

17. A process for producing a desized textile, comprising treating a sized textile with a polypeptide of claim 1.

18. A process for producing a dough product, comprising baking a dough in the presence of a polypeptide of claim 1.

* * * * *

UNITED STATES PATENT AND TRADEMARK OFFICE
CERTIFICATE OF CORRECTION

PATENT NO. : 8,039,241 B2
APPLICATION NO. : 12/755076
DATED : October 18, 2011
INVENTOR(S) : Lan et al.

Page 1 of 1

It is certified that error appears in the above-identified patent and that said Letters Patent is hereby corrected as shown below:

On the first page, in section (75) listing the inventors, please delete "Lan Tang" and insert --Tang Lan--.

On the first page, in section (60), which lists the related U.S. Application Data, please amend the paragraph as follows:

Continuation of application No. 12/036,806, filed on Feb. 25, 2008 now abandoned, which is a division of application No. 11/671,692, filed on Feb. 6, 2007, now abandoned, which is a ~~continuation~~ division of application No. 10/539,396, filed as application No. PCT/DK03/00882 on Dec. 16, 2003, now Pat. No. 7,189,552.

Signed and Sealed this
Twentieth Day of December, 2011

David J. Kappos
*Director of the United States Patent and Trademark Office*

SEQUENCE LISTING

<160> NUMBER OF SEQ ID NOS: 6

<210> SEQ ID NO 1
<211> LENGTH: 18
<212> TYPE: DNA
<213> ORGANISM: Artificial sequence
<220> FEATURE:
<223> OTHER INFORMATION: Primer AM298-CDSF

<400> SEQUENCE: 1
tatcatgaaa ttcagcat                18

<210> SEQ ID NO 2
<211> LENGTH: 19
<212> TYPE: DNA
<213> ORGANISM: Artificial sequence
<220> FEATURE:
<223> OTHER INFORMATION: Primer AM298-CDSR

<400> SEQUENCE: 2
agttcaaaat ggacaaagt               19

<210> SEQ ID NO 3
<211> LENGTH: 1438
<212> TYPE: DNA
<213> ORGANISM: Rhizomucor pusillus
<220> FEATURE:
<221> NAME/KEY: CDS
<222> LOCATION: (5)..(1417)
<220> FEATURE:
<221> NAME/KEY: sig_peptide
<222> LOCATION: (5)..(68)
<220> FEATURE:
<221> NAME/KEY: mat_peptide
<222> LOCATION: (68)..()

<400> SEQUENCE: 3

```
tatc atg aaa ttc agc atc tct ctc tcg gca gca att gta ctc ttc gcg      49
     Met Lys Phe Ser Ile Ser Leu Ser Ala Ala Ile Val Leu Phe Ala
         -20                 -15                 -10 gcc gca aca agc ctt gca agc cct ttg ccc caa cag cag cga tat ggc       97
Ala Ala Thr Ser Leu Ala Ser Pro Leu Pro Gln Gln Gln Arg Tyr Gly
     -5                  -1   1               5                  10 aaa aga gca act tcg gat gac tgg aaa agc aag gcc att tat cag ctg      145
Lys Arg Ala Thr Ser Asp Asp Trp Lys Ser Lys Ala Ile Tyr Gln Leu
             15                  20                  25 ctt aca gat cga ttt ggc cgc gcc gat gac tca aca agc aac tgc tct      193
Leu Thr Asp Arg Phe Gly Arg Ala Asp Asp Ser Thr Ser Asn Cys Ser
             30                  35                  40
```

| | | |
|---|---|---|
| aat tta tcc aac tac tgt ggt ggt acc tac gaa ggc att acg aag cat<br>Asn Leu Ser Asn Tyr Cys Gly Gly Thr Tyr Glu Gly Ile Thr Lys His<br>       45                 50              55 | 241 | |
| ctt gac tac att tcc ggt atg ggc ttt gat gct atc tgg ata tcg cca<br>Leu Asp Tyr Ile Ser Gly Met Gly Phe Asp Ala Ile Trp Ile Ser Pro<br>60                65                70 | 289 | |
| att ccc aag aac tcg gat gga ggc tac cac ggc tac tgg gct aca gat<br>Ile Pro Lys Asn Ser Asp Gly Gly Tyr His Gly Tyr Trp Ala Thr Asp<br>75                80              85              90 | 337 | |
| ttc tac caa cta aac agc aac ttt ggt gat gaa tcc cag ctc aaa gcg<br>Phe Tyr Gln Leu Asn Ser Asn Phe Gly Asp Glu Ser Gln Leu Lys Ala<br>              95              100           105 | 385 | |
| ctc atc cag gct gcc cat gaa cgt gac atg tat gtt atg ctt gat gtc<br>Leu Ile Gln Ala Ala His Glu Arg Asp Met Tyr Val Met Leu Asp Val<br>          110              115             120 | 433 | |
| gta gcc aat cat gca ggt ccc acc agc aat ggc tac tcg ggt tac aca<br>Val Ala Asn His Ala Gly Pro Thr Ser Asn Gly Tyr Ser Gly Tyr Thr<br>          125              130           135 | 481 | |
| ttc ggc gat gca agt tta tat cat cct aaa tgc acc ata gat tac aat<br>Phe Gly Asp Ala Ser Leu Tyr His Pro Lys Cys Thr Ile Asp Tyr Asn<br>140                145              150 | 529 | |
| gat cag acg tct att gag caa tgc tgg gtt gct gac gag ttg cct gat<br>Asp Gln Thr Ser Ile Glu Gln Cys Trp Val Ala Asp Glu Leu Pro Asp<br>155                160              165          170 | 577 | |
| att gac act gaa aat tct gac aac gtg gcc att ctc aac gac atc gtc<br>Ile Asp Thr Glu Asn Ser Asp Asn Val Ala Ile Leu Asn Asp Ile Val<br>                   175           180            185 | 625 | |
| tcc ggc tgg gtg ggt aac tat agc ttt gac ggc atc cgc att gat act<br>Ser Gly Trp Val Gly Asn Tyr Ser Phe Asp Gly Ile Arg Ile Asp Thr<br>              190              195           200 | 673 | |
| gtc aag cat att cgc aag gac ttt tgg aca ggc tac gca gaa gct gcc<br>Val Lys His Ile Arg Lys Asp Phe Trp Thr Gly Tyr Ala Glu Ala Ala<br>          205              210           215 | 721 | |
| ggc gta ttc gca act gga gag gtc ttc aat ggt gat ccg gcc tac gtt<br>Gly Val Phe Ala Thr Gly Glu Val Phe Asn Gly Asp Pro Ala Tyr Val<br>          220              225           230 | 769 | |
| gga cct tat caa aag tac ctg cca tct ctc atc aat tac cca atg tat<br>Gly Pro Tyr Gln Lys Tyr Leu Pro Ser Leu Ile Asn Tyr Pro Met Tyr<br>235                240              245          250 | 817 | |
| tac gct ttg aac gac gtc ttt gta tcc aaa agc aaa gga ttc agc cgc<br>Tyr Ala Leu Asn Asp Val Phe Val Ser Lys Ser Lys Gly Phe Ser Arg<br>                   255           260            265 | 865 | |
| atc agc gaa atg cta gga tca aat cgc aat gcg ttt gag gat acc agc<br>Ile Ser Glu Met Leu Gly Ser Asn Arg Asn Ala Phe Glu Asp Thr Ser<br>          270              275           280 | 913 | |
| gta ctt aca acg ttt gta gac aac cat gac aat ccg cgc ttc ttg aac<br>Val Leu Thr Thr Phe Val Asp Asn His Asp Asn Pro Arg Phe Leu Asn<br>          285              290           295 | 961 | |
| agt caa agc gac aag gct ctc ttc aag aac gct ctc aca tac gta ctg<br>Ser Gln Ser Asp Lys Ala Leu Phe Lys Asn Ala Leu Thr Tyr Val Leu<br>300                305              310 | 1009 | |
| cta ggt gaa ggc atc cca att gtg tat tat ggt tct gag caa ggt ttc<br>Leu Gly Glu Gly Ile Pro Ile Val Tyr Tyr Gly Ser Glu Gln Gly Phe<br>315                320              325          330 | 1057 | |
| agc gga gga gcg gat cct gct aac cgt gaa gtg ctg tgg acc acc aat<br>Ser Gly Gly Ala Asp Pro Ala Asn Arg Glu Val Leu Trp Thr Thr Asn<br>                   335           340            345 | 1105 | |
| tat gat aca tcc agc gat ctc tac caa ttt atc aag aca gtc aac agt<br>Tyr Asp Thr Ser Ser Asp Leu Tyr Gln Phe Ile Lys Thr Val Asn Ser<br>          350              355           360 | 1153 | |

-continued

```
gtc cgc atg aaa agc aac aag gcc gtc tac atg gat att tat gtt ggc    1201
Val Arg Met Lys Ser Asn Lys Ala Val Tyr Met Asp Ile Tyr Val Gly
    365                 370                 375 gac aat gct tac gcc ttc aag cac ggc gat gct ttg gtt gtt ctc aat    1249
Asp Asn Ala Tyr Ala Phe Lys His Gly Asp Ala Leu Val Val Leu Asn
380                 385                 390 aac tat gga tca ggt tcc aca aac caa gtc agc ttc agc gtt agt ggc    1297
Asn Tyr Gly Ser Gly Ser Thr Asn Gln Val Ser Phe Ser Val Ser Gly
395                 400                 405                 410 aag ttc gat agc ggc gca agc ctc atg gat att gtc agt aac att acc    1345
Lys Phe Asp Ser Gly Ala Ser Leu Met Asp Ile Val Ser Asn Ile Thr
                415                 420                 425 acc acg gtg tcc tcg gat gga aca gtc act ttc aac ctt aaa gat gga    1393
Thr Thr Val Ser Ser Asp Gly Thr Val Thr Phe Asn Leu Lys Asp Gly
            430                 435                 440 ctt ccg gct atc ttc acc tct gct taactttgtc cattttgaac t            1438
Leu Pro Ala Ile Phe Thr Ser Ala
            445                 450
```

<210> SEQ ID NO 4
<211> LENGTH: 471
<212> TYPE: PRT
<213> ORGANISM: Rhizomucor pusillus

<400> SEQUENCE: 4

```
Met Lys Phe Ser Ile Ser Leu Ser Ala Ala Ile Val Leu Phe Ala Ala
    -20                 -15                 -10

Ala Thr Ser Leu Ala Ser Pro Leu Pro Gln Gln Gln Arg Tyr Gly Lys
-5                  -1   1           5                  10

Arg Ala Thr Ser Asp Asp Trp Lys Ser Lys Ala Ile Tyr Gln Leu Leu
                15                  20                  25

Thr Asp Arg Phe Gly Arg Ala Asp Asp Ser Thr Ser Asn Cys Ser Asn
                30                  35                  40

Leu Ser Asn Tyr Cys Gly Gly Thr Tyr Glu Gly Ile Thr Lys His Leu
45                  50                  55

Asp Tyr Ile Ser Gly Met Gly Phe Asp Ala Ile Trp Ile Ser Pro Ile
60                  65                  70                  75

Pro Lys Asn Ser Asp Gly Gly Tyr His Gly Tyr Trp Ala Thr Asp Phe
                80                  85                  90

Tyr Gln Leu Asn Ser Asn Phe Gly Asp Glu Ser Gln Leu Lys Ala Leu
                95                 100                 105

Ile Gln Ala Ala His Glu Arg Asp Met Tyr Val Met Leu Asp Val Val
                110                 115                 120

Ala Asn His Ala Gly Pro Thr Ser Asn Gly Tyr Ser Gly Tyr Thr Phe
125                 130                 135

Gly Asp Ala Ser Leu Tyr His Pro Lys Cys Thr Ile Asp Tyr Asn Asp
140                 145                 150                 155

Gln Thr Ser Ile Glu Gln Cys Trp Val Ala Asp Glu Leu Pro Asp Ile
                160                 165                 170

Asp Thr Glu Asn Ser Asp Asn Val Ala Ile Leu Asn Asp Ile Val Ser
                175                 180                 185

Gly Trp Val Gly Asn Tyr Ser Phe Asp Gly Ile Arg Ile Asp Thr Val
            190                 195                 200

Lys His Ile Arg Lys Asp Phe Trp Thr Gly Tyr Ala Glu Ala Ala Gly
205                 210                 215

Val Phe Ala Thr Gly Glu Val Phe Asn Gly Asp Pro Ala Tyr Val Gly
220                 225                 230                 235
```

```
Pro Tyr Gln Lys Tyr Leu Pro Ser Leu Ile Asn Tyr Pro Met Tyr Tyr
            240                 245                 250

Ala Leu Asn Asp Val Phe Val Ser Lys Ser Lys Gly Phe Ser Arg Ile
            255                 260                 265

Ser Glu Met Leu Gly Ser Asn Arg Asn Ala Phe Glu Asp Thr Ser Val
            270                 275                 280

Leu Thr Thr Phe Val Asp Asn His Asp Asn Pro Arg Phe Leu Asn Ser
            285                 290                 295

Gln Ser Asp Lys Ala Leu Phe Lys Asn Ala Leu Thr Tyr Val Leu Leu
300                 305                 310                 315

Gly Glu Gly Ile Pro Ile Val Tyr Tyr Gly Ser Glu Gln Gly Phe Ser
            320                 325                 330

Gly Gly Ala Asp Pro Ala Asn Arg Glu Val Leu Trp Thr Thr Asn Tyr
            335                 340                 345

Asp Thr Ser Ser Asp Leu Tyr Gln Phe Ile Lys Thr Val Asn Ser Val
            350                 355                 360

Arg Met Lys Ser Asn Lys Ala Val Tyr Met Asp Ile Tyr Val Gly Asp
            365                 370                 375

Asn Ala Tyr Ala Phe Lys His Gly Asp Ala Leu Val Val Leu Asn Asn
380                 385                 390                 395

Tyr Gly Ser Gly Ser Thr Asn Gln Val Ser Phe Ser Val Ser Gly Lys
            400                 405                 410

Phe Asp Ser Gly Ala Ser Leu Met Asp Ile Val Ser Asn Ile Thr Thr
            415                 420                 425

Thr Val Ser Ser Asp Gly Thr Val Thr Phe Asn Leu Lys Asp Gly Leu
            430                 435                 440

Pro Ala Ile Phe Thr Ser Ala
    445                 450

<210> SEQ ID NO 5
<211> LENGTH: 32
<212> TYPE: DNA
<213> ORGANISM: Artificial sequence
<220> FEATURE:
<223> OTHER INFORMATION: Primer 168/R.p. amy3-forw

<400> SEQUENCE: 5
gaagatctac catgaaattc agcatctctc tc                                    32

<210> SEQ ID NO 6
<211> LENGTH: 30
<212> TYPE: DNA
<213> ORGANISM: Artificial sequence
<220> FEATURE:
<223> OTHER INFORMATION: Primer 169/R.p. amy4-rev

<400> SEQUENCE: 6
ccgctcgagt taagcagagg tgaagatagc                                       30
```